(12) United States Patent
Perret et al.

(10) Patent No.: US 9,534,012 B2
(45) Date of Patent: Jan. 3, 2017

(54) AFFINITY SUBSTRATE AND METHODS FOR SELECTIVELY PURIFYING A BLOOD PLASMA PROTEIN

(75) Inventors: Gerald Perret, Choisy le Roi (FR); Michel Nogre, Vanves (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 364 days.

(21) Appl. No.: 13/201,690

(22) PCT Filed: Feb. 19, 2010

(86) PCT No.: PCT/FR2010/050294
§ 371 (c)(1),
(2), (4) Date: Aug. 16, 2011

(87) PCT Pub. No.: WO2010/094901
PCT Pub. Date: Aug. 26, 2010

(65) Prior Publication Data
US 2012/0122179 A1    May 17, 2012

(30) Foreign Application Priority Data

Feb. 19, 2009 (FR) ..................... 09 51083

(51) Int. Cl.
| | |
|---|---|
| *C12N 9/96* | (2006.01) |
| *C07K 1/22* | (2006.01) |
| *C07K 14/745* | (2006.01) |
| *C12N 9/64* | (2006.01) |
| *C12N 15/115* | (2010.01) |

(52) U.S. Cl.
CPC .............. *C07K 1/22* (2013.01); *C07K 14/745* (2013.01); *C12N 9/647* (2013.01); *C12N 15/115* (2013.01); *C12N 2310/16* (2013.01); *C12N 2320/00* (2013.01)

(58) Field of Classification Search
None
See application file for complete search history.

(56) References Cited

U.S. PATENT DOCUMENTS

| | | | |
|---|---|---|---|
| 5,986,062 A | 11/1999 | Ohmura et al. | |
| 6,117,996 A | 9/2000 | Lowe et al. | |
| 7,312,325 B2 * | 12/2007 | Sullenger et al. | 536/24.5 |

FOREIGN PATENT DOCUMENTS

| | | |
|---|---|---|
| EP | 0 570 916 A2 | 11/1993 |
| EP | 0 612 761 A1 | 8/1994 |
| JP | 06-100592 A | 4/1994 |
| JP | 06-245789 A | 9/1994 |
| WO | 2006/023831 A2 | 3/2006 |
| WO | 2007/058592 A1 | 5/2007 |
| WO | 2008/099077 A2 | 8/2008 |

OTHER PUBLICATIONS

Qiang Z. et al: "Aptamer-Based Affinity Chromatography Assays for Thrombin" Analytical Chemistry, vol. 80, No. 19, Oct. 1, 2008 (Oct. 1, 2008), pp. 7586-7593, XP002557962.
Liu Xuemei et al: "RNA aptamers specific for bovine thrombin" Journal of Molecular Recognition, vol. 16, No. 1, Jan. 1, 2003 (Jan. 1, 2003), pp. 23-27, XP002479553.
International Search Report, dated Jun. 2, 2010, in PCT/FR2010/050294.
Zhao et al., "Aptamer-Modified Monolithic Capillary Chromatography for Protein Separation and Detection", Analytical Chemistry, vol. 80, No. 10, May 15, 2008, pp. 3915-3920.
Boese et al., "In vitro selection and characterization of cellulose-binding DNA aptamers," Nucleic Acids Research, vol. 35, No. 19, Sep. 2007, pp. 6378-6388.
Cole et al., "Affinity Capture and Detection of Immunoglobulin E in Human Serum using an Aptamer-Modified Surface in Matrix Assisted Laser Desorption/Ionization Mass Spectrometry," Analytical Chemistry, vol. 79, No. 1, Jan. 2007, pp. 273-279.
Connor et al., "Aptamer stationary phase for protein capture in affinity capillary chromatography," Journal of Chromatography A, vol. 1111, 2006, pp. 115-119.
Deng et al., "Aptamer affinity chromatography for rapid assay of adenosine in microdialysis samples collected in vivo," Journal of Chromatography A, vol. 1005, 2003, pp. 123-130.
Higashimoto et al., "In vitro selection of DNA aptamers that block toxic effects of AGE on cultured retinal pericytes" Microvasc. Res., vol. 74, No. 1, Jul. 2007, pp. 65-69.
Murphy et al., "An improved method for the in vitro evolution of aptamers and application in protein detection and purification," Nucleic Acids Research, vol. 31, No. 18, 2003, 8 pages.
Romig et al., "Aptamer affinity chromatography: combinatorial chemistry applied to protein purification," Journal of Chromatography B, vol. 731, 1999, pp. 275-284.
Yao et al., "Aptamer-based piezoelectric quartz crystal microbalance biosensor array for the quantification of IgE," Biosensors and Bioelectronics, vol. 24, Jan. 4, 2009, pp. 2499-2503.
Zhao, et al.; "Apatamer-Based Affinity Chromatographic Assays for Thrombin"; Analytical Chemistry, vol. 80, No. 19; Oct. 1, 2008; pp. 7586-7593.
Miyakawa, S., et al.; Structural and molecular basis for hyperspecificity of RNA aptamer to human immunoglobulin G; RNA (2008), 14: pp. 1154-1163.

* cited by examiner

*Primary Examiner* — Hope Robinson
(74) *Attorney, Agent, or Firm* — Foley & Lardner LLP

(57) ABSTRACT

An affinity substrate for the selective binding of a protein of blood plasma includes a solid substrate material on which are immobilized deoxyribonucleic aptamers specifically binding with the plasma protein.

14 Claims, 9 Drawing Sheets

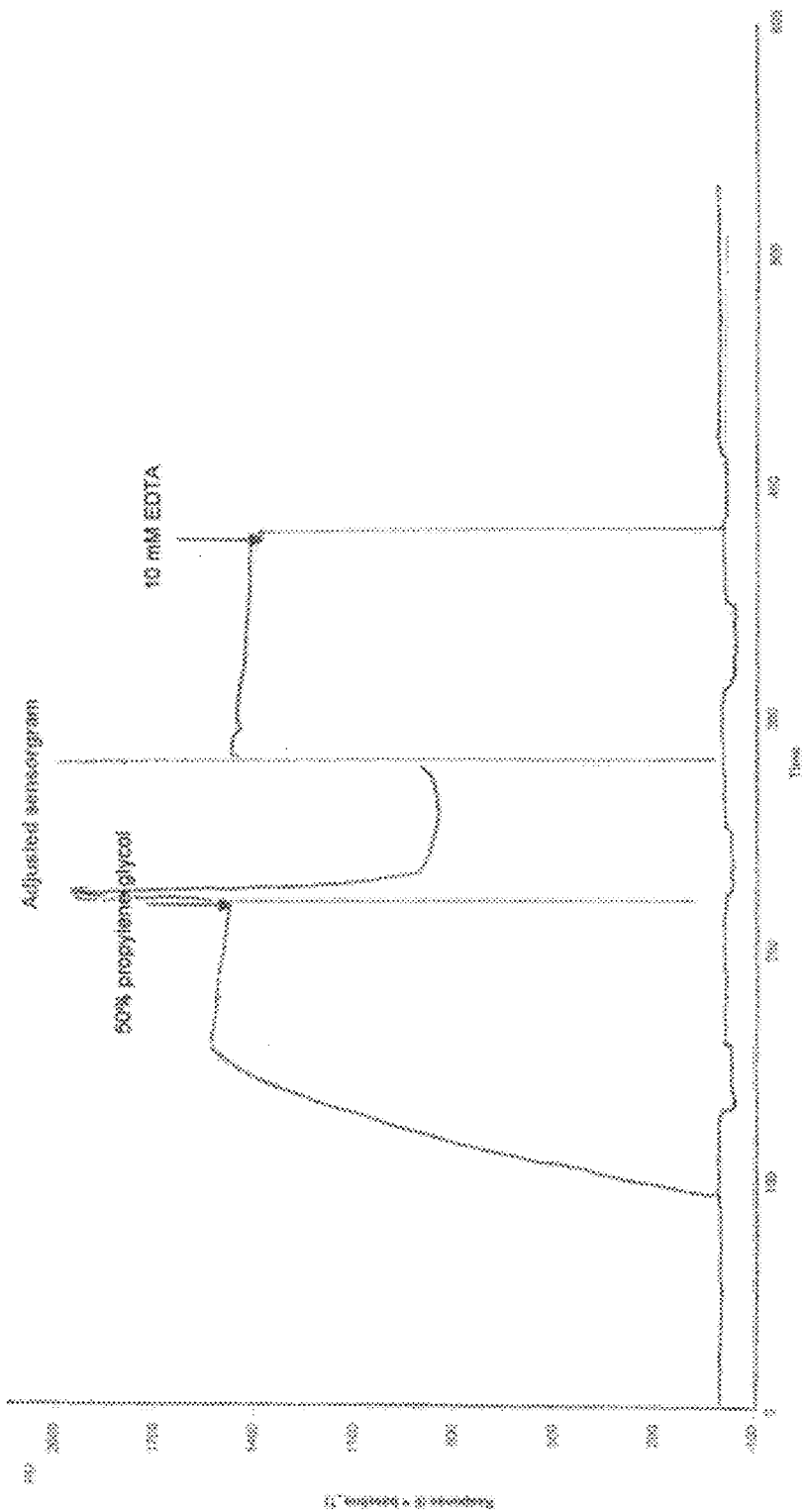

SEQUENCE LISTING

<160> NUMBER OF SEQ ID NOS: 101

<210> SEQ ID NO 1
<211> LENGTH: 18
<212> TYPE: DNA
<213> ORGANISM: artificial sequence
<220> FEATURE:
<223> OTHER INFORMATION: aptamer

<400> SEQUENCE: 1
gggagatagc cacgacct                                          18

<210> SEQ ID NO 2
<211> LENGTH: 18
<212> TYPE: DNA
<213> ORGANISM: artificial sequence
<220> FEATURE:
<223> OTHER INFORMATION: aptamer

<400> SEQUENCE: 2
tccaggctgt gcgaaagc                                          18

<210> SEQ ID NO 3
<211> LENGTH: 44
<212> TYPE: DNA
<213> ORGANISM: artificial sequence
<220> FEATURE:
<223> OTHER INFORMATION: aptamer

<400> SEQUENCE: 3
ccgcacacca cgcgcattag cccgcgcaca cgacttgaag tagc             44

<210> SEQ ID NO 4
<211> LENGTH: 44
<212> TYPE: DNA
<213> ORGANISM: artificial sequence
<220> FEATURE:
<223> OTHER INFORMATION: aptamer

<400> SEQUENCE: 4
ccgcacacca cgcgcattag cccgcgcaca cgacttgaag tagc             44

<210> SEQ ID NO 5
<211> LENGTH: 43
<212> TYPE: DNA
<213> ORGANISM: artificial sequence
<220> FEATURE:
<223> OTHER INFORMATION: aptamer

<400> SEQUENCE: 5
cgcacaccac gcgcattagc ccgcgcacac gacttgaagt agc              43

<210> SEQ ID NO 6
<211> LENGTH: 44
<212> TYPE: DNA
<213> ORGANISM: artificial sequence
<220> FEATURE:
<223> OTHER INFORMATION: aptamer

<400> SEQUENCE: 6
ccgcacacca cgcgcatgaa cccgcgcaca cgacttgaag tagc             44

<210> SEQ ID NO 7
<211> LENGTH: 44
<212> TYPE: DNA
<213> ORGANISM: artificial sequence
<220> FEATURE:
<223> OTHER INFORMATION: aptamer

<400> SEQUENCE: 7
ccgcacacca cgcgcatgaa cccgcgcaca cgacttgaag tagc             44

<210> SEQ ID NO 8

```
<211> LENGTH: 44
<212> TYPE: DNA
<213> ORGANISM: artificial sequence
<220> FEATURE:
<223> OTHER INFORMATION: aptamer

<400> SEQUENCE: 8
ccgcacacca cgcgcatgaa cccgcgcaca cgacttgaag tagc                         44

<210> SEQ ID NO 9
<211> LENGTH: 44
<212> TYPE: DNA
<213> ORGANISM: artificial sequence
<220> FEATURE:
<223> OTHER INFORMATION: aptamer

<400> SEQUENCE: 9
ccgcacacca cgcgcatgaa cccgcgcaca cgacttgaag tagc                         44

<210> SEQ ID NO 10
<211> LENGTH: 44
<212> TYPE: DNA
<213> ORGANISM: artificial sequence
<220> FEATURE:
<223> OTHER INFORMATION: aptamer

<400> SEQUENCE: 10
acgcacacca cgcgcatgaa cccgcgcaca cgacttgaag tagc                         44

<210> SEQ ID NO 11
<211> LENGTH: 44
<212> TYPE: DNA
<213> ORGANISM: artificial sequence
<220> FEATURE:
<223> OTHER INFORMATION: aptamer

<400> SEQUENCE: 11
ccgcacacca cgcgcatgag cccgcgcaca cgacttgaag tagc                         44

<210> SEQ ID NO 12
<211> LENGTH: 44
<212> TYPE: DNA
<213> ORGANISM: artificial sequence
<220> FEATURE:
<223> OTHER INFORMATION: aptamer

<400> SEQUENCE: 12
ccgcacacca cgcgcatgag cccgcgcaca cgacttgaag tagc                         44

<210> SEQ ID NO 13
<211> LENGTH: 44
<212> TYPE: DNA
<213> ORGANISM: artificial sequence
<220> FEATURE:
<223> OTHER INFORMATION: aptamer

<400> SEQUENCE: 13
ccgcacacca cgcgcatgag cccgcgcaca cgacttgaag tagc                         44

<210> SEQ ID NO 14
<211> LENGTH: 45
<212> TYPE: DNA
<213> ORGANISM: artificial sequence
<220> FEATURE:
<223> OTHER INFORMATION: aptamer

<400> SEQUENCE: 14
```
gccgcacacc acgcgcatga gcccgcgcac acgacttgaa gtagc        45

<210> SEQ ID NO 15
<211> LENGTH: 43
<212> TYPE: DNA
<213> ORGANISM: artificial sequence
<220> FEATURE:
<223> OTHER INFORMATION: aptamer

<400> SEQUENCE: 15
cgcacaccac gcgcatgagc ccgcgcacac gacttgaagt agc        43

<210> SEQ ID NO 16
<211> LENGTH: 44
<212> TYPE: DNA
<213> ORGANISM: artificial sequence
<220> FEATURE:
<223> OTHER INFORMATION: aptamer

<400> SEQUENCE: 16
tcgcacacca cgcgcatgag cccgcgcaca cgacttgaag tagc        44

<210> SEQ ID NO 17
<211> LENGTH: 44
<212> TYPE: DNA
<213> ORGANISM: artificial sequence
<220> FEATURE:
<223> OTHER INFORMATION: aptamer

<400> SEQUENCE: 17
acgcacacca cgcgcatgag cccgcgcaca cgacttgaag tagc        44

<210> SEQ ID NO 18
<211> LENGTH: 44
<212> TYPE: DNA
<213> ORGANISM: artificial sequence
<220> FEATURE:
<223> OTHER INFORMATION: aptamer

<400> SEQUENCE: 18
acgcacacca cgcgcatgag cccgcgcaca cgacttgaag tagc        44

<210> SEQ ID NO 19
<211> LENGTH: 43
<212> TYPE: DNA
<213> ORGANISM: artificial sequence
<220> FEATURE:
<223> OTHER INFORMATION: aptamer
<220> FEATURE:
<221> NAME/KEY: misc_feature
<222> LOCATION: (19)..(19)
<223> OTHER INFORMATION: n is a, c, g, or t

<400> SEQUENCE: 19
cgcacaccac gcgcatganc ccgcgcacac gacttgaagt agc        43

<210> SEQ ID NO 20
<211> LENGTH: 44
<212> TYPE: DNA
<213> ORGANISM: artificial sequence
<220> FEATURE:
<223> OTHER INFORMATION: aptamer

<400> SEQUENCE: 20
ccgcacacca cgcgcataat cccgcgcaca cgacttgaag tagc        44

<210> SEQ ID NO 21
<211> LENGTH: 44
<212> TYPE: DNA
<213> ORGANISM: artificial sequence
<220> FEATURE:
<223> OTHER INFORMATION: aptamer

<400> SEQUENCE: 21
ccgcacacca cgcgcatgac cccgcgcaca cgacttgaag tagc                44

<210> SEQ ID NO 22
<211> LENGTH: 44
<212> TYPE: DNA
<213> ORGANISM: artificial sequence
<220> FEATURE:
<223> OTHER INFORMATION: aptamer

<400> SEQUENCE: 22
ccgcacacca cgcgcatgac cccgcgcaca cgacttgaag tagc                44

<210> SEQ ID NO 23
<211> LENGTH: 43
<212> TYPE: DNA
<213> ORGANISM: artificial sequence
<220> FEATURE:
<223> OTHER INFORMATION: aptamer

<400> SEQUENCE: 23
cgcacaccac gcgcgtgacc ccgcgcacac gacttgaagt agc                 43

<210> SEQ ID NO 24
<211> LENGTH: 44
<212> TYPE: DNA
<213> ORGANISM: artificial sequence
<220> FEATURE:
<223> OTHER INFORMATION: aptamer

<400> SEQUENCE: 24
ccgcacacca cgcgcattaa cccgcgcaca cggcttggag tagc                44

<210> SEQ ID NO 25
<211> LENGTH: 44
<212> TYPE: DNA
<213> ORGANISM: artificial sequence
<220> FEATURE:
<223> OTHER INFORMATION: aptamer

<400> SEQUENCE: 25
tcgcacacta cgcgcatgaa cccgcgcaca cgacttgaag tagc                44

<210> SEQ ID NO 26
<211> LENGTH: 44
<212> TYPE: DNA
<213> ORGANISM: artificial sequence
<220> FEATURE:
<223> OTHER INFORMATION: aptamer

<400> SEQUENCE: 26
tcgcacacta cgcgcatgaa cccgcgcaca cgacttgaag tagc                44

<210> SEQ ID NO 27
<211> LENGTH: 43
<212> TYPE: DNA
<213> ORGANISM: artificial sequence
<220> FEATURE:
<223> OTHER INFORMATION: aptamer

<400> SEQUENCE: 27
cgcacactac gcgcatgaac ccgcgcacac gacttgaagt agc        43

<210> SEQ ID NO 28
<211> LENGTH: 45
<212> TYPE: DNA
<213> ORGANISM: artificial sequence
<220> FEATURE:
<223> OTHER INFORMATION: aptamer

<400> SEQUENCE: 28
gccgcacact acgcgcatga gcccgcgcac acgacttgaa gtagc      45

<210> SEQ ID NO 29
<211> LENGTH: 44
<212> TYPE: DNA
<213> ORGANISM: artificial sequence
<220> FEATURE:
<223> OTHER INFORMATION: aptamer

<400> SEQUENCE: 29
tcgcacacta cgcgcatgag cccgcgcaca cgacttgaag tagc       44

<210> SEQ ID NO 30
<211> LENGTH: 44
<212> TYPE: DNA
<213> ORGANISM: artificial sequence
<220> FEATURE:
<223> OTHER INFORMATION: aptamer

<400> SEQUENCE: 30
ccgcacacta cgcgcatgat cccgcgcaca cgacttgaag tagc       44

<210> SEQ ID NO 31
<211> LENGTH: 44
<212> TYPE: DNA
<213> ORGANISM: artificial sequence
<220> FEATURE:
<223> OTHER INFORMATION: aptamer

<400> SEQUENCE: 31
ccgcacacta cgcgcatgat cccgcgcaca cgacttgaag tagc       44

<210> SEQ ID NO 32
<211> LENGTH: 44
<212> TYPE: DNA
<213> ORGANISM: artificial sequence
<220> FEATURE:
<223> OTHER INFORMATION: aptamer

<400> SEQUENCE: 32
ctgcacacta cgcgcatgat cccgcgcaca cgacttgaag tagc       44

<210> SEQ ID NO 33
<211> LENGTH: 44
<212> TYPE: DNA
<213> ORGANISM: artificial sequence
<220> FEATURE:
<223> OTHER INFORMATION: aptamer

<400> SEQUENCE: 33
ccgcacgcta cgcgcatgaa cccgcgcaca cgacttgaag tagc       44

<210> SEQ ID NO 34

<210> SEQ ID NO 34
<211> LENGTH: 44
<212> TYPE: DNA
<213> ORGANISM: artificial sequence
<220> FEATURE:
<223> OTHER INFORMATION: aptamer

<400> SEQUENCE: 34
ccgcacacta cgcgcacgaa cccgcgcaca cgacttgaag tagc         44

<210> SEQ ID NO 35
<211> LENGTH: 44
<212> TYPE: DNA
<213> ORGANISM: artificial sequence
<220> FEATURE:
<223> OTHER INFORMATION: aptamer

<400> SEQUENCE: 35
tcgcacacta cgcgcatgac cccgcgcaca cgacttgaag tagc         44

<210> SEQ ID NO 36
<211> LENGTH: 43
<212> TYPE: DNA
<213> ORGANISM: artificial sequence
<220> FEATURE:
<223> OTHER INFORMATION: aptamer

<400> SEQUENCE: 36
agcacaccac gcgcataaac ccgcgcacac gacttgaagt agc          43

<210> SEQ ID NO 37
<211> LENGTH: 44
<212> TYPE: DNA
<213> ORGANISM: artificial sequence
<220> FEATURE:
<223> OTHER INFORMATION: aptamer

<400> SEQUENCE: 37
gagcacacca cgcgcatgaa cccgcgcaca cgacttgaag tagc         44

<210> SEQ ID NO 38
<211> LENGTH: 46
<212> TYPE: DNA
<213> ORGANISM: artificial sequence
<220> FEATURE:
<223> OTHER INFORMATION: aptamer

<400> SEQUENCE: 38
gctagcacac cacgcgcatg aacccgcgca cacgacttga agtacc       46

<210> SEQ ID NO 39
<211> LENGTH: 44
<212> TYPE: DNA
<213> ORGANISM: artificial sequence
<220> FEATURE:
<223> OTHER INFORMATION: aptamer

<400> SEQUENCE: 39
acgcacacca cgcgcatgaa cccgcgcaca tgacttgaag tagc         44

<210> SEQ ID NO 40
<211> LENGTH: 44
<212> TYPE: DNA
<213> ORGANISM: artificial sequence
<220> FEATURE:
<223> OTHER INFORMATION: aptamer

<400> SEQUENCE: 40
ccgcacacca cgcgcattag cccgcgcaca cgacttgaag ttaa                 44

<210> SEQ ID NO 41
<211> LENGTH: 44
<212> TYPE: DNA
<213> ORGANISM: artificial sequence
<220> FEATURE:
<223> OTHER INFORMATION: aptamer

<400> SEQUENCE: 41
ccggagacgc gcagctccta tacatgcgca catgacttga agtc                 44

<210> SEQ ID NO 42
<211> LENGTH: 44
<212> TYPE: DNA
<213> ORGANISM: artificial sequence
<220> FEATURE:
<223> OTHER INFORMATION: aptamer

<400> SEQUENCE: 42
ccggagacgc gcagctccta tacatgcgca catgacttga agtc                 44

<210> SEQ ID NO 43
<211> LENGTH: 44
<212> TYPE: DNA
<213> ORGANISM: artificial sequence
<220> FEATURE:
<223> OTHER INFORMATION: aptamer

<400> SEQUENCE: 43
cttgagacgc gcatttgcta tacatgcgca cgtgacttga agtc                 44

<210> SEQ ID NO 44
<211> LENGTH: 44
<212> TYPE: DNA
<213> ORGANISM: artificial sequence
<220> FEATURE:
<223> OTHER INFORMATION: aptamer

<400> SEQUENCE: 44
cttgagacgc gcatttgcta tacatgcgca cgtgacttga agtc                 44

<210> SEQ ID NO 45
<211> LENGTH: 43
<212> TYPE: DNA
<213> ORGANISM: artificial sequence
<220> FEATURE:
<223> OTHER INFORMATION: aptamer
<220> FEATURE:
<221> NAME/KEY: misc_feature
<222> LOCATION: (13)..(13)
<223> OTHER INFORMATION: n is a, c, g, or t

<400> SEQUENCE: 45
ctgagacgcg canttgctat acatgcgcac atgacttgaa gtc                  43

<210> SEQ ID NO 46
<211> LENGTH: 46
<212> TYPE: DNA
<213> ORGANISM: artificial sequence
<220> FEATURE:
<223> OTHER INFORMATION: aptamer

<400> SEQUENCE: 46
ctggagacgc gcagttgctg tacatgcgca catgacttga agtagc               46

<210> SEQ ID NO 47
<211> LENGTH: 44
<212> TYPE: DNA
<213> ORGANISM: artificial sequence
<220> FEATURE:
<223> OTHER INFORMATION: aptamer

<400> SEQUENCE: 47
gtggagacgc gcatttgctg tacatgcgca catgactaga agtc        44

<210> SEQ ID NO 48
<211> LENGTH: 44
<212> TYPE: DNA
<213> ORGANISM: artificial sequence
<220> FEATURE:
<223> OTHER INFORMATION: aptamer

<400> SEQUENCE: 48
caggagacgc gcatttgttg tacatgcgca catgactaga agtc        44

<210> SEQ ID NO 49
<211> LENGTH: 44
<212> TYPE: DNA
<213> ORGANISM: artificial sequence
<220> FEATURE:
<223> OTHER INFORMATION: aptamer

<400> SEQUENCE: 49
ctggagacgc gcagttgttg tacacgcgca catgactaga agtc        44

<210> SEQ ID NO 50
<211> LENGTH: 44
<212> TYPE: DNA
<213> ORGANISM: artificial sequence
<220> FEATURE:
<223> OTHER INFORMATION: aptamer

<400> SEQUENCE: 50
ctggagacgc gcagttgcta cacacgcgca catgactaga agtc        44

<210> SEQ ID NO 51
<211> LENGTH: 44
<212> TYPE: DNA
<213> ORGANISM: artificial sequence
<220> FEATURE:
<223> OTHER INFORMATION: aptamer

<400> SEQUENCE: 51
ctggagacgc gcacttcctt tacatgcgca catgactaga agtc        44

<210> SEQ ID NO 52
<211> LENGTH: 44
<212> TYPE: DNA
<213> ORGANISM: artificial sequence
<220> FEATURE:
<223> OTHER INFORMATION: aptamer

<400> SEQUENCE: 52
ctggagacgc gcagttgctt tacatgcgca catgactaga agtc        44

<210> SEQ ID NO 53
<211> LENGTH: 44
<212> TYPE: DNA
<213> ORGANISM: artificial sequence
<220> FEATURE:
<223> OTHER INFORMATION: aptamer

<400> SEQUENCE: 53
ctggagacgc gcagttgctg tacatgcgca catgactaga agtc                44

<210> SEQ ID NO 54
<211> LENGTH: 44
<212> TYPE: DNA
<213> ORGANISM: artificial sequence
<220> FEATURE:
<223> OTHER INFORMATION: aptamer

<400> SEQUENCE: 54
ctggagacgc gcagttgctg tacatgcgca catgactaga agtc                44

<210> SEQ ID NO 55
<211> LENGTH: 44
<212> TYPE: DNA
<213> ORGANISM: artificial sequence
<220> FEATURE:
<223> OTHER INFORMATION: aptamer

<400> SEQUENCE: 55
ctggggacgc gcagttgctg tacatgcgca catgactaga agtc                44

<210> SEQ ID NO 56
<211> LENGTH: 44
<212> TYPE: DNA
<213> ORGANISM: artificial sequence
<220> FEATURE:
<223> OTHER INFORMATION: aptamer

<400> SEQUENCE: 56
ctggagacgc gcagttacca tacgtgcgca catgactaga agtc                44

<210> SEQ ID NO 57
<211> LENGTH: 44
<212> TYPE: DNA
<213> ORGANISM: artificial sequence
<220> FEATURE:
<223> OTHER INFORMATION: aptamer

<400> SEQUENCE: 57
ctggagacgc gcagttgctg tacgtgcgca catgactaga agtc                44

<210> SEQ ID NO 58
<211> LENGTH: 44
<212> TYPE: DNA
<213> ORGANISM: artificial sequence
<220> FEATURE:
<223> OTHER INFORMATION: aptamer

<400> SEQUENCE: 58
agtctccatg ttgcgaaccg aatggtaagg ggatcgtaca ctac                44

<210> SEQ ID NO 59
<211> LENGTH: 44
<212> TYPE: DNA
<213> ORGANISM: artificial sequence
<220> FEATURE:
<223> OTHER INFORMATION: aptamer

<400> SEQUENCE: 59
agtctccatg ttgcgaaccg aatggtaagg ggatcgtaca ctac                44

<210> SEQ ID NO 60

```
<211> LENGTH: 44
<212> TYPE: DNA
<213> ORGANISM: artificial sequence
<220> FEATURE:
<223> OTHER INFORMATION: aptamer

<400> SEQUENCE: 60
agactccatg atgcgaaccg aatggtaagg gaatcgtaca atac                          44

<210> SEQ ID NO 61
<211> LENGTH: 44
<212> TYPE: DNA
<213> ORGANISM: artificial sequence
<220> FEATURE:
<223> OTHER INFORMATION: aptamer

<400> SEQUENCE: 61
agactccatg atgcgaaccg aatggtaagg gaatcgtaca atac                          44

<210> SEQ ID NO 62
<211> LENGTH: 44
<212> TYPE: DNA
<213> ORGANISM: artificial sequence
<220> FEATURE:
<223> OTHER INFORMATION: aptamer

<400> SEQUENCE: 62
agactccatt atgcgaaccg aatggtaagg gaatcgtaca atac                          44

<210> SEQ ID NO 63
<211> LENGTH: 44
<212> TYPE: DNA
<213> ORGANISM: artificial sequence
<220> FEATURE:
<223> OTHER INFORMATION: aptamer

<400> SEQUENCE: 63
agactccatg atgcgaaccg aatggtaagg gaatcgtaca gtac                          44

<210> SEQ ID NO 64
<211> LENGTH: 44
<212> TYPE: DNA
<213> ORGANISM: artificial sequence
<220> FEATURE:
<223> OTHER INFORMATION: aptamer

<400> SEQUENCE: 64
agactccatg atgcgaaccg aatggtaagg gaatcgtaca gtac                          44

<210> SEQ ID NO 65
<211> LENGTH: 44
<212> TYPE: DNA
<213> ORGANISM: artificial sequence
<220> FEATURE:
<223> OTHER INFORMATION: aptamer

<400> SEQUENCE: 65
agactccatg atgcgaaccg aatggtaagg gaatcgtaca atgc                          44

<210> SEQ ID NO 66
<211> LENGTH: 44
<212> TYPE: DNA
<213> ORGANISM: artificial sequence
<220> FEATURE:
<223> OTHER INFORMATION: aptamer

<400> SEQUENCE: 66
```
agactccatg atgcgaaccg aatggtaagg gaatcgtaca atgc       44

<210> SEQ ID NO 67
<211> LENGTH: 44
<212> TYPE: DNA
<213> ORGANISM: artificial sequence
<220> FEATURE:
<223> OTHER INFORMATION: aptamer

<400> SEQUENCE: 67
agactccatg atgcgaaccg aatggtaagg gaatcgtaca atgc       44

<210> SEQ ID NO 68
<211> LENGTH: 44
<212> TYPE: DNA
<213> ORGANISM: artificial sequence
<220> FEATURE:
<223> OTHER INFORMATION: aptamer

<400> SEQUENCE: 68
agactccatg atgcgaaccg aatggtaagg gaatcgtacg acac       44

<210> SEQ ID NO 69
<211> LENGTH: 44
<212> TYPE: DNA
<213> ORGANISM: artificial sequence
<220> FEATURE:
<223> OTHER INFORMATION: aptamer

<400> SEQUENCE: 69
agactccatg gtgcgaaccg aatggtaagg gaatcgtaca acac       44

<210> SEQ ID NO 70
<211> LENGTH: 44
<212> TYPE: DNA
<213> ORGANISM: artificial sequence
<220> FEATURE:
<223> OTHER INFORMATION: aptamer

<400> SEQUENCE: 70
tgactccatg atgcgaaccg aatggtaagg gaatcgtaca acac       44

<210> SEQ ID NO 71
<211> LENGTH: 44
<212> TYPE: DNA
<213> ORGANISM: artificial sequence
<220> FEATURE:
<223> OTHER INFORMATION: aptamer

<400> SEQUENCE: 71
agactccatg atgcgaaccg aatggttagg gaatcgtaca atac       44

<210> SEQ ID NO 72
<211> LENGTH: 44
<212> TYPE: DNA
<213> ORGANISM: artificial sequence
<220> FEATURE:
<223> OTHER INFORMATION: aptamer

<400> SEQUENCE: 72
agactccatg atgcgaaccg aatggttagg gaatcgtaca atac       44

<210> SEQ ID NO 73
<211> LENGTH: 44
<212> TYPE: DNA

```
<213> ORGANISM: artificial sequence
<220> FEATURE:
<223> OTHER INFORMATION: aptamer

<400> SEQUENCE: 73
agactccatg atgcgaaccg aatggttagg gaatcgtaca acac         44

<210> SEQ ID NO 74
<211> LENGTH: 44
<212> TYPE: DNA
<213> ORGANISM: artificial sequence
<220> FEATURE:
<223> OTHER INFORMATION: aptamer

<400> SEQUENCE: 74 agacccatg atgcgaaccg aatggttagg gaatcgtaca gtac          44

<210> SEQ ID NO 75
<211> LENGTH: 44
<212> TYPE: DNA
<213> ORGANISM: artificial sequence
<220> FEATURE:
<223> OTHER INFORMATION: aptamer

<400> SEQUENCE: 75
agaccccctg atgcgaaccg aatggttagg gaatcgtaca atac         44

<210> SEQ ID NO 76
<211> LENGTH: 44
<212> TYPE: DNA
<213> ORGANISM: artificial sequence
<220> FEATURE:
<223> OTHER INFORMATION: aptamer

<400> SEQUENCE: 76
agactccatg atgcgaaccg aatggtaagg gaatcgcact gtac         44

<210> SEQ ID NO 77
<211> LENGTH: 44
<212> TYPE: DNA
<213> ORGANISM: artificial sequence
<220> FEATURE:
<223> OTHER INFORMATION: aptamer

<400> SEQUENCE: 77
agactccaag atgcgaaccg aatggtaagg gaatcgtaca gtac         44

<210> SEQ ID NO 78
<211> LENGTH: 44
<212> TYPE: DNA
<213> ORGANISM: artificial sequence
<220> FEATURE:
<223> OTHER INFORMATION: aptamer

<400> SEQUENCE: 78
agaccccgtg atgcgaaccg aatggtaagg gaatcgcaca atac         44

<210> SEQ ID NO 79
<211> LENGTH: 44
<212> TYPE: DNA
<213> ORGANISM: artificial sequence
<220> FEATURE:
<223> OTHER INFORMATION: aptamer

<400> SEQUENCE: 79
agactccccg atgcgaaccg aatggtaagg gaatcgtacg atgc         44
```

<210> SEQ ID NO 80
<211> LENGTH: 44
<212> TYPE: DNA
<213> ORGANISM: artificial sequence
<220> FEATURE:
<223> OTHER INFORMATION: aptamer

<400> SEQUENCE: 80 agacccatg acgcgaaccg aatggtaagg gaatcgtaca atgc        44

<210> SEQ ID NO 81
<211> LENGTH: 44
<212> TYPE: DNA
<213> ORGANISM: artificial sequence
<220> FEATURE:
<223> OTHER INFORMATION: aptamer

<400> SEQUENCE: 81 agacccatg atgcgaaccg aatggtaagg gaatcgtact acac        44

<210> SEQ ID NO 82
<211> LENGTH: 44
<212> TYPE: DNA
<213> ORGANISM: artificial sequence
<220> FEATURE:
<223> OTHER INFORMATION: aptamer

<400> SEQUENCE: 82 agacccatg atgcgaaccg aatggtaagg ggatcgtaca accc        44

<210> SEQ ID NO 83
<211> LENGTH: 43
<212> TYPE: DNA
<213> ORGANISM: artificial sequence
<220> FEATURE:
<223> OTHER INFORMATION: aptamer

<400> SEQUENCE: 83
agactccatg atgcgaaccg aatggtaagg gaatcataca ccc        43

<210> SEQ ID NO 84
<211> LENGTH: 44
<212> TYPE: DNA
<213> ORGANISM: artificial sequence
<220> FEATURE:
<223> OTHER INFORMATION: aptamer

<400> SEQUENCE: 84
agactccatg atgctaaccg aatggttagg gaatcgtacg acgc        44

<210> SEQ ID NO 85
<211> LENGTH: 45
<212> TYPE: DNA
<213> ORGANISM: artificial sequence
<220> FEATURE:
<223> OTHER INFORMATION: aptamer

<400> SEQUENCE: 85
atgcagccag ccgcagtgta agtgaatgca gacatggtct aagtg        45

<210> SEQ ID NO 86
<211> LENGTH: 81
<212> TYPE: DNA
<213> ORGANISM: artificial sequence
<220> FEATURE:

<223> OTHER INFORMATION: aptamer

<400> SEQUENCE: 86
gggagatagc cacgacctat gcagccagcc gcagtgtaag tgaatgcaga catggtctaa     60
gtgtccaggc tgtgcgaaag c     81

<210> SEQ ID NO 87
<211> LENGTH: 43
<212> TYPE: DNA
<213> ORGANISM: artificial sequence
<220> FEATURE:
<223> OTHER INFORMATION: aptamer

<400> SEQUENCE: 87
taagccgctg cgtattatag ctgaatgccc ctaatgggaa gtg     43

<210> SEQ ID NO 88
<211> LENGTH: 44
<212> TYPE: DNA
<213> ORGANISM: artificial sequence
<220> FEATURE:
<223> OTHER INFORMATION: aptamer

<400> SEQUENCE: 88
catgccgctg cgtattatag ctgaatgccc cacaatggga agtg     44

<210> SEQ ID NO 89
<211> LENGTH: 44
<212> TYPE: DNA
<213> ORGANISM: artificial sequence
<220> FEATURE:
<223> OTHER INFORMATION: aptamer

<400> SEQUENCE: 89
caagccgctg cgtattatag ctgaatgccc cataatggga agtg     44

<210> SEQ ID NO 90
<211> LENGTH: 43
<212> TYPE: DNA
<213> ORGANISM: artificial sequence
<220> FEATURE:
<223> OTHER INFORMATION: aptamer

<400> SEQUENCE: 90
caagccgctg cgtatttagc tgaatgcccc ctaatgggaa gtg     43

<210> SEQ ID NO 91
<211> LENGTH: 44
<212> TYPE: DNA
<213> ORGANISM: artificial sequence
<220> FEATURE:
<223> OTHER INFORMATION: aptamer

<400> SEQUENCE: 91
ccagccgctg cgtatcatag ctgaatgccc cataatggga agtg     44

<210> SEQ ID NO 92
<211> LENGTH: 43
<212> TYPE: DNA
<213> ORGANISM: artificial sequence
<220> FEATURE:
<223> OTHER INFORMATION: aptamer

<400> SEQUENCE: 92
caagccgctg cgtaatatag ctgaatgccc cataatggaa gtg     43

<210> SEQ ID NO 93
<211> LENGTH: 44
<212> TYPE: DNA
<213> ORGANISM: artificial sequence
<220> FEATURE:
<223> OTHER INFORMATION: aptamer

<400> SEQUENCE: 93
caagcctctg cgtattatag ctgaatgctc cttaatggta agtg        44

<210> SEQ ID NO 94
<211> LENGTH: 44
<212> TYPE: DNA
<213> ORGANISM: artificial sequence
<220> FEATURE:
<223> OTHER INFORMATION: aptamer

<400> SEQUENCE: 94
caagccgctg cgtattatag ctgaatgctc cttaatggta agtg        44

<210> SEQ ID NO 95
<211> LENGTH: 44
<212> TYPE: DNA
<213> ORGANISM: artificial sequence
<220> FEATURE:
<223> OTHER INFORMATION: aptamer

<400> SEQUENCE: 95
ccaggcgctg cgtatcatag ctgaatgctc cttaacggta agtg        44

<210> SEQ ID NO 96
<211> LENGTH: 44
<212> TYPE: DNA
<213> ORGANISM: artificial sequence
<220> FEATURE:
<223> OTHER INFORMATION: aptamer

<400> SEQUENCE: 96
caagccgctg cgttttatag ctgaatgctc ctcaatggta agtg        44

<210> SEQ ID NO 97
<211> LENGTH: 44
<212> TYPE: DNA
<213> ORGANISM: artificial sequence
<220> FEATURE:
<223> OTHER INFORMATION: aptamer

<400> SEQUENCE: 97
caagccgctg cgttttatag ctgaatgctc catcttggta agtg        44

<210> SEQ ID NO 98
<211> LENGTH: 44
<212> TYPE: DNA
<213> ORGANISM: artificial sequence
<220> FEATURE:
<223> OTHER INFORMATION: aptamer
<220> FEATURE:
<221> NAME/KEY: misc_feature
<222> LOCATION: (18)..(18)
<223> OTHER INFORMATION: n is a, t, g, or c

<400> SEQUENCE: 98
gtgcagccag ccgcagtnta agtgagctga ttgaagcatg aggg        44

<210> SEQ ID NO 99

```
<211> LENGTH: 45
<212> TYPE: DNA
<213> ORGANISM: artificial sequence
<220> FEATURE:
<223> OTHER INFORMATION: aptamer

<400> SEQUENCE: 99
atgcagccag ccgcagtgta agtgaatgca gacatggtct aagtg            45

<210> SEQ ID NO 100
<211> LENGTH: 45
<212> TYPE: DNA
<213> ORGANISM: artificial sequence
<220> FEATURE:
<223> OTHER INFORMATION: aptamer

<400> SEQUENCE: 100
ccagcagagc cgcagtttca gtgaatgcag atcatggtct aagtg            45

<210> SEQ ID NO 101
<211> LENGTH: 80
<212> TYPE: DNA
<213> ORGANISM: artificial sequence
<220> FEATURE:
<223> OTHER INFORMATION: aptamer

<400> SEQUENCE: 101
gggagatagc cacgacctcg cacatgactt gaagttaaac gcgaattaca aacccagccc      60
cctccaggct gtgcgaaagc                                                  80
```

AFFINITY SUBSTRATE AND METHODS FOR SELECTIVELY PURIFYING A BLOOD PLASMA PROTEIN

CROSS-REFERENCE TO RELATED PATENT APPLICATIONS

This application is a U.S. national stage of PCT/FR2010/050294, filed Feb. 19, 2010, which claims priority to French Patent Application No. 0951083, filed Feb. 19, 2009, all of which are hereby incorporated by reference in their entirety.

FIELD OF THE INVENTION

The present invention relates to the field of the purification of blood plasma proteins that can be used as active ingredients of medicaments.

PRIOR ART

Blood plasma proteins have for a long time constituted active ingredients for medicaments. Among the blood plasma proteins used as active ingredients of medicaments, mention may in particular be made of factor VII, factor VIII, thrombin or else von Willebrand factor.

Until recently, plasma proteins were exclusively obtained by purification from human blood plasma. Over the past few years, some plasma proteins have been obtained in the form of recombinant proteins produced in body fluids of transgenic mammals, for example in the milk of transgenic mammals.

In all cases, the starting material containing the plasma protein to be purified consists of a material of complex constitution, in which the protein of interest is present in combination with a very large number of substances, including proteins, lipids, carbohydrates, amino acids, mineral salts, cell debris and metabolic waste such as urea, uric acid or bilirubin.

The development of a method for purifying a plasma protein is therefore a complex task, given the health and regulatory characteristics required for the marketing of a medicament for human use.

It is understood that, in a medicament for human or veterinary use, the plasma protein used as active ingredient should be present in a highly purified form and not be associated with undesirable substances capable of being detrimental to the organism, including other plasma proteins, or else degradation products of the abovementioned proteins.

Methods for purifying various plasma proteins are known, including methods for purifying factor VIII, anti-thrombin-III, plasminogen, factor VII or else von Willebrand factor.

All the known methods comprise a succession of selective-separation steps based on steps of protein precipitation, of passage over chromatography substrates followed by sequential-elution steps, deep-filtration steps, ultrafiltration steps or else concentration steps.

It is specified that the development of methods for purifying coagulation proteins, whether these methods are entirely novel, or whether these methods are adaptations, even minimal adaptations, of known methods, requires long research and numerous controls of conformity of the successive intermediate products, in order to be sure that the final product will be obtained with a great purity, in a nonmodified form, substantially free of undesirable substances and both sterile and apyrogenic. In particular, for plasma proteins having an enzymatic activity, for instance factors VII, VIII and XI, it is essential that the purified final protein not be activated. However, the activation of a coagulation protein is liable to be induced during any one of the purification steps, including during the chromatography steps, if predetermined set conditions, for example quality of the filters or of the chromatographic substrate used, salt concentration or else temperature, are not adhered to.

The aforementioned at least partially explains why the known methods do not comprise an affinity chromatography step, based on the principle of specific immobilization of the plasma protein of interest on a ligand grafted to the chromatographic substrate, and then recovery of the purified protein in the chromatography eluate.

The absence of an affinity chromatography purification step in methods for purifying proteins of therapeutic interest is also explained by the drawbacks of this technique in which detachment of a part of the ligand molecules grafted to the affinity substrate is observed, said ligand molecules being found associated with the purified therapeutic protein in the volume of the eluate. It is understood that the presence, in a medicament comprising a purified plasma protein, of constituent substances of a chromatography substrate, which are possibly detrimental to the organism, may jeopardize the health of the patient and is prohibited by the medical regulations.

Although the known methods for purifying plasma proteins are satisfactory, there is a need in the prior art for alternative methods or methods that are improved compared with the existing methods.

SUMMARY OF THE INVENTION

The invention relates to an affinity substrate for selectively binding a blood plasma protein, comprising a solid substrate material on which deoxyribonucleic aptamers which bind specifically to said plasma protein are immobilized.

A subject of the invention is also a method for immobilizing a blood plasma protein on a substrate, comprising a step during which a sample containing said plasma protein is brought into contact with an affinity substrate.

The invention also relates to a method for purifying a blood plasma protein, comprising the following steps:
 a) bringing a sample containing a blood plasma protein into contact with an affinity substrate as defined above, in order to form complexes between (i) the deoxyribonucleic aptamers immobilized on said affinity substrate and (ii) said plasma protein, and
 b) releasing the protein from the complexes formed in step a), and
 c) recovering said blood plasma protein in a purified form.

It also relates to a purified composition of a recombinant human plasma protein comprising at least 99.9% by weight of said recombinant human protein and which is substantially free of nonhuman proteins.

DESCRIPTION OF THE FIGURES

In FIG. 6, peak No. 1 corresponds to the fraction of the starting product which was not retained on the column. Peak No. 2 corresponds to the elution fraction.

FIG. 9 represents the curves of binding of the Mapt2 immobilized aptamer to the recombinant human factor VII produced in the milk of a transgenic rabbit. The arrows correspond to the time of the various injections, respectively from left to right on FIG. 9: 1: 50% propylene glycol; 2: EDTA at 10 mM.

DETAILED DESCRIPTION OF THE INVENTION

Figure 1:
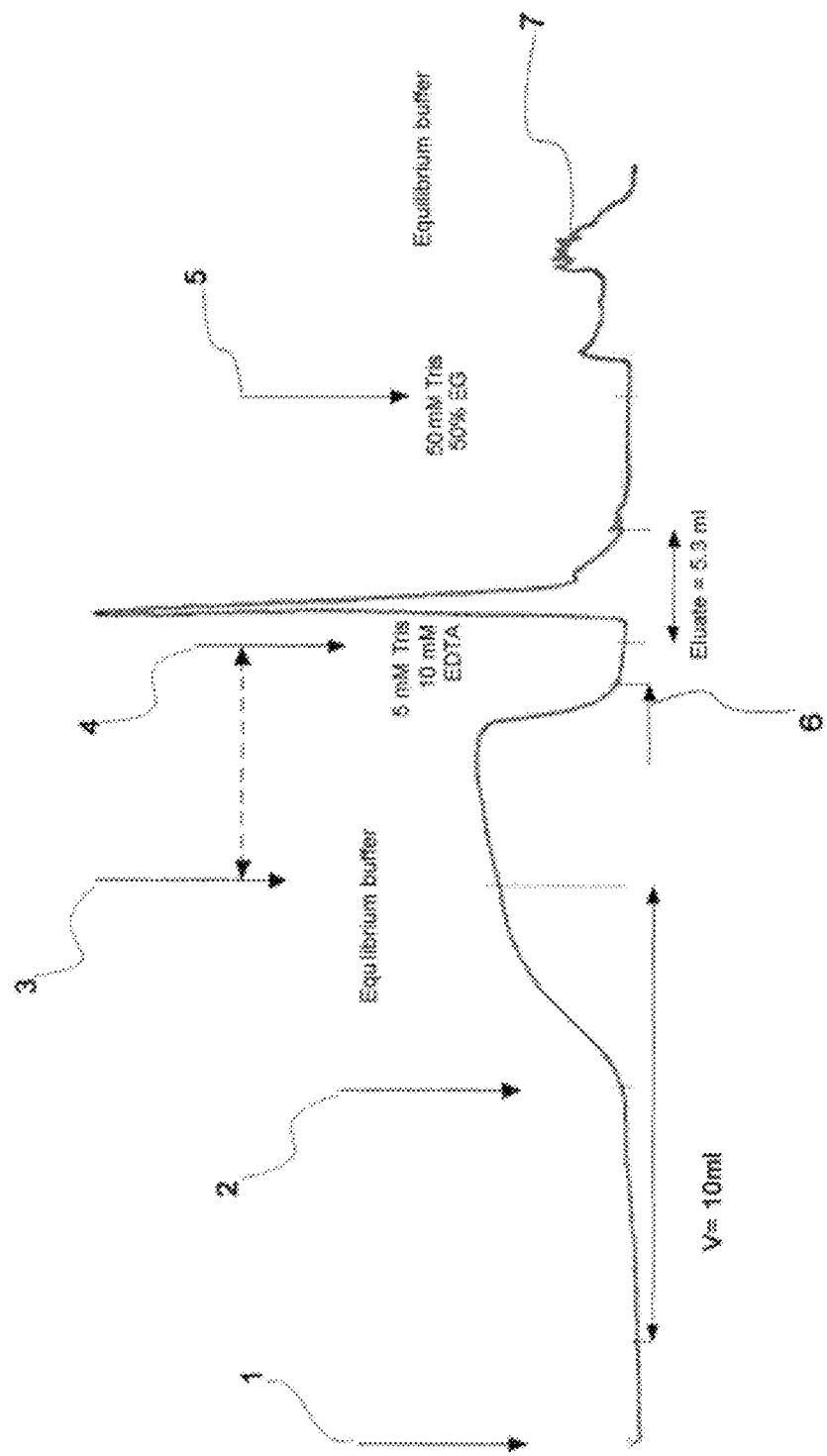
FIG. 1 illustrates a chromatography profile obtained during the implementation of the method for purifying a recombinant human factor VII produced in rabbit milk, with the affinity substrate in which anti-human FVII nucleic aptamers are immobilized. Along the x-axis: the time; along the y-axis: the absorbance value (OD) at 254 nanometers.

After long research, the applicant has developed a method for purifying blood plasma proteins, comprising a step of chromatography during which there is specific binding of the protein of interest to a ligand preimmobilized on the chromatography substrate, and then of release of the protein of interest retained on said substrate and recovery of the purified protein in the eluate volume.

More specifically, according to the invention, a method is provided for purifying blood plasma proteins, comprising a step of specific binding of the plasma protein of interest to a substrate on which deoxyribonucleic aptamers which bind specifically to said protein of interest are immobilized, followed by a step of recovery of said purified protein of interest.

Surprisingly, it has been shown, according to the invention, that affinity chromatography substrates on which are immobilized deoxyribonucleic aptamers specific for the plasma protein of interest, i.e. including in the form of immobilized compounds comprising such deoxyribonucleic aptamers, can be used successfully in methods for obtaining plasma proteins that can be used as active ingredients of a medicament.

Surprisingly, it is shown according to the invention that it is possible to fabricate an affinity substrate as defined in the present description by using deoxyribonucleic acid (DNA) aptamers, which are nevertheless considered in the prior art to be ligand nucleic acids that are not easy to use, and the specificity of which for the target protein is less than the specificity of the RNA molecule of corresponding sequence. In particular, it is accepted in the prior art that ligand DNAs have less flexibility than the corresponding RNA and that, consequently, they are less capable than the ligand RNAs of undergoing conformational changes. It is recalled that, when a nucleic aptamer binds to the target protein, a conformational change occurs. It has also been described that, the faster the conformational change of the nucleic aptamer, the higher the affinity of said nucleic aptamer for the target protein (Michaud et al., 2003, Anal Chem, vol. 76: 1015-1020; Brumbt et al., 2005, Anal Chem, vol. 77: 1993-1998).

It has also been shown that the affinity substrate of the invention makes it possible to purify coagulation proteins from starting media of complex composition, such as a plasma composition enriched in human factor IX and a milk from an animal that is transgenic for human factor IX, with great specificity of binding to said coagulation protein of interest.

It has also been shown that the affinity substrate of the invention makes it possible to selectively purify a human coagulation protein from a starting medium also comprising a nonhuman orthologous protein, for example from a milk of an animal that is transgenic for human factor IX, said milk also comprising factor IX produced naturally by said transgenic animal, it being possible for said factor IX produced naturally by said transgenic animal (or endogenous FIX) to be, for example, a porcine FIX.

It has also been shown that the affinity substrate of the invention makes it possible to selectively purify a human coagulation protein from a starting medium also comprising a nonhuman orthologous protein, for example from a milk of an animal that is transgenic for human factor VII, said milk also comprising factor VII produced naturally by said transgenic animal, it being possible for said factor VII produced naturally by said transgenic animal (or endogenous FVII) to be, for example, a rabbit FVII.

The present invention relates to an affinity substrate for selectively binding a blood plasma protein, comprising a solid substrate material on which deoxyribonucleic aptamers which bind specifically to said plasma protein, including in the form of compounds comprising such deoxyribonucleic aptamers, are immobilized.

The molecules of deoxyribonucleic aptamer which bind specifically to the plasma protein of interest, and also the compounds comprising such deoxyribonucleic aptamers, constitute sites for specific binding of said target protein which are carried by said solid substrate material.

The term "deoxyribonucleic aptamers" encompasses single-stranded deoxyribonucleic acids having a length of 5 to 120 nucleotides and which bind specifically to a blood plasma protein. The expression "compounds comprising a deoxyribonucleic aptamer" also encompasses compounds which comprise, in their structure, said deoxyribonucleic acids defined above. Thus, the compounds comprising a deoxyribonucleic acid which binds specifically to a human or mammalian plasma protein encompass compounds in which said deoxyribonucleic acid is included in a structure comprising a biotin molecule.

It has been shown, according to the invention, that an affinity substrate as defined above allows efficient immobilization of the plasma protein of interest, which may also be referred to as "target protein" in the present description.

An affinity substrate as defined above has a high capacity for adsorption of the target protein, since bringing the solid substrate into contact with a liquid solution containing the plasma protein to be purified makes it possible to saturate at least 50 percent of the target sites carried by the solid substrate.

It has also been shown, according to the invention, that the plasma protein molecules which are specifically bound to the deoxyribonucleic aptamer molecules can subsequently be eluted from the affinity substrate with a good yield, of at least 75 percent.

Furthermore, it has been shown that the affinity substrate of the invention has a high specificity for the plasma protein of interest, since said plasma protein can be found with a degree of purity ranging up to 99.95 percent by weight, relative to the total weight of the proteins contained in the eluate.

As is illustrated in the examples, an increase of two orders of magnitude in the purity of the coagulation protein of interest can further be obtained with an affinity substrate according to the invention, using, as starting product, a composition comprising the target coagulation protein at a high degree of purity, for example at more than 98% by weight, relative to the total weight of the proteins contained in said starting product. It is specified that such an increase in purity is obtained including when the impurities present in the starting product have structural or physicochemical characteristics very close to those of the target coagulation protein that it is desired to purify.

Importantly, it has been shown that the above characteristics of high absorption capacity, of good yield and of high specificity of the affinity substrate of the invention are obtained in particular for the purification of the plasma protein of interest from a starting medium of complex composition, such as blood plasma or else a biological fluid of a mammal that is transgenic for said plasma protein of interest.

It has also been shown that the immobilization of the nucleic aptamers on the solid substrate material is irreversible and long-lasting, since the presence of deoxyribonucleic aptamers detached from the substrate is not detectable in the eluate solution.

In particular, it has been shown that the affinity substrate of the invention can be "regenerated" by elimination of the proteins that have remained bound to the substrate after elution, very many times without significant impairment of (i) its capacity for absorption of the target plasma protein, (ii) its specificity with respect to said target protein, or else (iii) its absence of release of the deoxyribonucleic aptamers immobilized on the solid substrate material. Furthermore, the regeneration of the affinity substrate of the invention can be carried out according to known techniques and with known regenerating agents, such as urea.

The deoxyribonucleic acids used as ligands of the plasma protein of interest have many advantages. By virtue of their oligonucleotide nature, the aptamers have a weak immunogenicity and a high resistance to stringent physicochemical conditions (presence of urea, of DMSO, of a very acidic or very basic pH, use of organic solvents or of a high temperature) which allow varied strategies for controlling health safety, in particular safety with respect to viruses or non-conventional pathogenic agents, in the context of use as an affinity ligand. In addition, they are highly selective. Finally, as already mentioned, the production of deoxyribonucleic aptamers involves relatively limited costs.

Thus, the combination of above characteristics of the affinity substrate of the invention bring about the ability of said affinity substrate to be used as a means for purifying a blood plasma protein, since said affinity substrate makes it possible to carry out methods for purifying a plasma protein having a very high degree of purity, said affinity substrate does not detectably release undesirable substances, in particular deoxyribonucleic aptamer molecules, into the solution of eluate containing the purified plasma protein, the possible detachment of deoxyribonucleic aptamer molecules does not lead to drawbacks for human health, the binding and then the elution of the plasma protein of interest on the affinity substrate, when it is a plasma protein with enzymatic activity, does not lead to the formation of detectable amounts of the activated form of said plasma protein, said affinity substrate is relatively inexpensive to produce, in particular owing to the low costs of deoxyribonucleic aptamer production, and the use of said affinity substrate for purifying a plasma protein is itself relatively inexpensive owing to the longevity of said substrate, due in particular to the possibility of regenerating it many times, and over a long period of time.

In addition, as has already been mentioned, the affinity substrate of the invention is capable of selectively binding, in a reversible manner, the target plasma protein with a good yield and good specificity, in methods of purification from media of complex constitution, in particular from media conventionally used on the industrial scale, such as human plasma or culture media or biological fluids containing said protein of interest.

Furthermore, as will be detailed later in the present description, the affinity substrate of the invention is suitable for the treatment of large volumes of solution containing the plasma protein of interest. The affinity substrate of the invention thus constitutes a tool for purifying a blood plasma protein which is perfectly suitable for use on the industrial scale.

Other advantages of the affinity substrate according to the invention will subsequently be specified in the present description, either in relation to the description of the affinity substrate itself, or in relation to the methods for purifying a plasma protein in which said affinity substrate can be used.

To the applicant's knowledge, the present invention describes for the first time an affinity substrate comprising immobilized deoxyribonucleic aptamers, for purifying a blood plasma protein under conditions for use on the industrial scale. A variety of nucleic aptamers specific for thrombin, for factor VII and for factor IX is, moreover, known in the prior art (see PCT Application No. WO 02/26932). However, to the applicant's knowledge, the use of deoxyribonucleic aptamers for the production of affinity substrates which can be used on an industrial scale in processes for purifying plasma proteins has never been described in the prior art.

The term "selective binding" is intended to mean, for the purposes of the present description, the specific noncovalent binding of the plasma protein of interest to the constituent immobilized deoxyribonucleic acids of the affinity substrate, which is reversible by bringing the affinity substrate, on which noncovalent complexes between said deoxyribonucleic acids and said protein of interest are formed, into contact with a solution of suitable composition, which can also be referred to as elution solution.

The term "plasma protein" is intended to mean, according to the invention, any protein, especially any protein of industrial or therapeutic interest, contained in blood plasma. Blood plasma proteins encompass albumin, alpha/macroglobulin, antichyomotrypsin, antithrombin, antitrypsin, Apo A, Apo B, Apo C, Apo D, Apo E, Apo F, Apo G, beta XIIa, C1-inhibitor, C-reactive protein, C7, C1r, C1s, C2, C3, C4, C4bP, C5, C6, C1q, C8, C9, carboxypeptidase N, ceruloplasmin, factor B, factor D, factor H, factor I, factor IX, factor V, factor VII, factor VIIa, factor VIII, factor X, factor XI, factor XII, factor XIII, fibrinogen, fibronectin, haptoglobin, hemopexin, heparin cofactor II, histidine-rich GP, IgA, IgD, IgE, IgG, ITI, IgM, kininase II, kininogen HPM, lysozyme, PAI 2, PAI 1, PCI, plasmin, plasmin inhibitor, plasminogen, prealbumin, prokallikrein, properdin, protease nexin INH, protein C, protein S, protein Z, prothrombin, TFPI, thiol-proteinase, thrombomodulin, tissue factor (TF), TPA, transcolabamin II, transcortin, transferrin, vitronectin and von Willebrand factor.

In particular, the plasma proteins encompass the coagulation proteins, that is to say the plasma proteins involved in the chain of cascade reactions resulting in the formation of a blood clot. The coagulation proteins encompass factor I (fibrinogen), factor II (prothrombin), factor V (proaccelerin), factor VII (proconvertin), factor VIII (anti-hemophilic factor A), factor IX (anti-hemophilic factor B), factor X (Stuart factor), factor XI (Rosenthal factor or PTA), factor XII (Hageman factor), factor XIII (fibrin-stabilizing factor or FSF), PK (Prekallikrein), HMWK (high-molecular-weight kininogen), tissue thromboplastin, heparin cofactor II (Hal), protein C (PC), thrombomodulin (TM), protein S (PS), von Willebrand factor (vWF) and tissue factor pathway inhibitor (TFPI), or else tissue factors.

In some embodiments, the plasma protein consists of a coagulation protein with enzymatic activity.

The coagulation proteins with enzymatic activity encompass factor II (prothrombin), factor VII (proconvertin), factor IX (anti-hemophilic factor B), factor X (Stuart factor), factor XI (Rosenthal factor or PTA), factor XII (Hageman factor), factor XIII (fibrin-stabilizing factor or FSF) and PK (Prekallikrein).

In some preferred embodiments, the plasma protein consists of a natural or recombinant human plasma protein.

In preferred embodiments, the plasma protein is natural or recombinant human factor VII.

Generally, the solid substrates on which the aptamers of the invention can be immobilized encompass any type of substrate having the structure and the composition commonly found for filter substrates, membranes, etc. The solid substrates encompass in particular resins, affinity chromatography column resins, polymer beads, magnetic beads, paramagnetic beads, substrate materials of filter membranes, etc. The solid substrates also in particular encompass materials based on glass or on metal, such as steel, gold, silver, aluminum, copper, silicon, glass or ceramic. The solid substrates also in particular encompass polymer materials, such as a polyethylene, a polypropylene, a polyamide, a polyvinylidene fluoride, and combinations thereof.

In some embodiments, the solid substrate may be coated with a material which facilitates attachment, binding, complex formation, immobilization or interaction with the aptamers, or with the compounds comprising said aptamers.

In some embodiments, the solid substrate is a glass slide of which the surface is coated with a layer of gold, with a layer having undergone a treatment by carboxymethylation, with a layer of dextran, of collagen, of avidin, of streptavidin, etc.

In this way, the aptamers according to the invention, or the compounds comprising the aptamers according to the invention, can be immobilized on the solid substrate by means of an attachment coating, as, for example, described above, either by chemical reaction with the creation of covalent bonds, or by association via noncovalent bonds, such as hydrogen bonds, electrostatic forces, Van der Waals forces, etc.

The examples describe embodiments of an affinity substrate according to the invention in which the deoxyribonucleic aptamers are immobilized, by means of the compounds in the structure of which they are included, via noncovalent bonds to the solid substrate material.

In the examples, affinity substrates comprising a solid substrate material at the surface of which streptavidin molecules are grafted are in particular described, the deoxyribonucleic aptamers being included in the structure of compounds comprising aptamers coupled, at one of their ends, to a biotin molecule, and said aptamers being immobilized on said solid substrate material by noncovalent immobilization between the streptavidin molecules of the substrate material and the biotin molecules of the compounds comprising said deoxyribonucleic aptamers.

In the examples, an embodiment of an affinity substrate comprising a substrate material on which streptavidin molecules are grafted is described. Such solid substrate materials are readily commercially available.

The expression "deoxyribonucleic acids which bind specifically to a plasma protein", or "aptamers" or "nucleic aptamers" is intended to mean DNA (deoxyribonucleic acid) molecules having the capacity to bind to a given plasma protein of interest which is greater than the capacity to bind to any other protein.

In some embodiments, the constituent nucleic aptamers of the affinity substrate according to the invention have the capacity to bind to a given human plasma protein which is greater than the capacity to bind to any other human protein.

In some embodiments, the nucleic aptamers according to the invention have in particular the capacity to bind to a given human plasma protein, which is greater than the capacity to bind to any other homologous plasma protein encoded by the genome of a nonhuman mammal. By way of illustration, a nucleic aptamer specific for human factor VII, which can be used in an affinity substrate of the invention, has a capacity to bind to human factor VII which is greater than the capacity to bind to factor VII originating from a nonhuman mammal, including the rabbit factor VII.

For the purpose of the present description, a first deoxyribonucleic nucleic aptamer has a capacity to bind to human factor VII/VIIa which is greater than that of a second deoxyribonucleic aptamer of equivalent mass, when, by using any one of the above binding detection techniques and under the same test conditions, a statistically significant higher binding signal value is obtained with the first deoxyribonucleic aptamer, compared with that obtained with the second deoxyribonucleic aptamer. By way of illustration, when the binding detection technique used is the Biacore® technique, a first deoxyribonucleic aptamer has a capacity to bind to human factor VII/VIIa which is greater than that of a second deoxyribonucleic aptamer of equivalent mass, when the resonance signal value for the first deoxyribonucleic aptamer, irrespective of the resonance measurement unit expressed, is statistically higher than the resonance signal value measured for the second deoxyribonucleic aptamer. Two "statistically" distinct measurement values encompass two values which have, between them, a difference greater than the measurement error of the binding detection technique used.

Preferentially, a deoxyribonucleic aptamer of an affinity substrate of the invention has a strong affinity for the target plasma protein. Preferentially, said deoxyribonucleic aptamer has a Kd value, with respect to said target plasma protein, of less than 500 nM. The Kd value can be measured according to the Biacore® technique.

By way of illustration, it has been shown that the nucleic aptamer comprising the sequence SEQ ID NO: 86 has a capacity to bind to human factor VII/VIIa which is significantly greater than its capacity for binding to any factor VII/VIIa originating from a nonhuman mammal. In particular, 1 although an aptamer comprising the nucleic acid of SEQ ID NO: 86 has a strong capacity to bind to any type of human factor VII/VIIa, including a natural factor VII/VIIa. or a recombinant factor VII/VIIa, it has a weak or zero capacity to bind to a factor VII/VIIa. encoded by the genome of a nonhuman mammal, including a rabbit factor VII/VIIa.

More specifically, for the aptamer comprising the nucleic acid of sequence SEQ ID NO: 86 it has been determined, according to the Biacore® technique, that the value for the capacity for binding to human factor VII/VIIa, expressed as the dissociation constant Kd, is approximately 100 nM. Furthermore, said nucleic aptamer has a binding capacity which is identical both with respect to human plasma factor VII/VIIa and to recombinant human factor VII/VIIa, for example produced in a transgenic rabbit.

It has also been shown that the complexes between an aptamer comprising the nucleic acid of sequence SEQ ID NO: 86 and a human factor VII/VIIa are stoichiometric, i.e. the ratio of the number of molecules of nucleic acid of sequence SEQ ID NO: 86 to the number of molecules of human factor VII/VIIa that are complexed is approximately 1:1, and can be in particular 1:1.

As has already been mentioned above, the affinity substrate of the invention can be used in a step of a method for purifying a recombinant human plasma protein produced by a nonhuman transgenic mammal. In such embodiments of a method for purifying a plasma protein, the complex starting medium comprises the recombinant human protein as a mixture with numerous proteins produced naturally by said transgenic mammal, including, as appropriate, the plasma protein homologous to the recombinant human protein. It is understood that, in such embodiments, it is advantageous for the constituent nucleic aptamers of the affinity substrate of the invention to bind selectively to the human protein of interest, and not to bind, under the same operating conditions, to the homologous protein naturally produced by the nonhuman mammal.

In these particular embodiments of the constituent nucleic aptamers of the affinity substrate of the invention, the capacity of said aptamers to bind "specifically" to the human plasma protein of interest can also be expressed as the ratio of the dissociation constants Kd, respectively for the human protein and for the nonhuman mammalian homologous protein.

According to yet another characteristic of a constituent nucleic aptamer of the affinity substrate according to the invention, the capacity of said nucleic aptamer to bind specifically to the human plasma protein can also be expressed by the following condition (A):

$$\text{human Kd/nonhuman Kd} < 0.01 \quad (A),$$

in which:
"human Kd" is the dissociation constant of a nucleic aptamer for said human protein, expressed in molar units, and
"nonhuman Kd" is the dissociation constant of said nucleic aptamer for the nonhuman homologous protein, expressed in the same molar units.

Preferentially, for optimum use of the affinity substrate of the invention in methods for purifying a recombinant human plasma protein, a nucleic aptamer which binds specifically to said recombinant human protein can also be defined by a human Kd/nonhuman Kd ratio of less than 0.005.

The constituent nucleic aptamers of the affinity substrate of the invention can be prepared according to the technique called SELEX. The term "aptamer" as used encompasses a molecule of single-stranded deoxyribonucleic acid (DNA), capable of binding specifically to a protein. Aptamers generally comprise between 5 and 120 nucleotides and can be selected in vitro according to a method known as SELEX (Systematic Evolution of Ligands by Exponential Enrichment), which was initially described in particular in PCT application No. WO 1991/019813. The SELEX method for selecting aptamers consists, as regards obtaining the DNA aptamers used according to the invention, in bringing a protein into contact with a combinatorial library of deoxyribonucleic acids (in general 1015 molecules); the deoxyribonucleic acids which do not bind to the target are eliminated, the deoxyribonucleic acids which bind to the target are isolated and amplified. The method is repeated until the solution is sufficiently enriched with the deoxyribonucleic acids having a good affinity for the protein of interest (Tuerk and Gold, "Systematic evolution of ligands by exponential enrichment: RNA ligands to bacteriophage T4 DNA polymerase" (1990) Science, 249(4968): 505-10 and Ellington and Szostak, "In vitro selection of RNA molecules that bind specific ligands", (1990) Nature August 30; 346(6287):818-22). Other examples of the SELEX method are given in documents EP 0 786 469, EP 668 931, EP 1 695 978 and EP 1 493 825, the teachings of which can be reproduced in the implementation of the method for selecting a deoxyribonucleic aptamer used according to the invention.

For its use in a means for purifying human factor VII/VIIa, a deoxyribonucleic acid which binds specifically to a plasma protein of interest is preferentially included in a chemical structure, also called "compound" in the present description, which also comprises a spacer means and, where appropriate, a means of immobilization on a solid substrate.

In some embodiments, the deoxyribonucleic aptamer is included in the structure of a compound of formula (I) below:

$$[FIX]_x\text{-}[SPAC]_y\text{-}[APT] \quad (I), \text{ in which:}$$

[FIX] signifies a compound for immobilization on a substrate,

[SPAC] signifies a spacer chain,
[APT] signifies a deoxyribonucleic acid which binds specifically to a plasma protein, also denoted deoxyribonucleic aptamer,
x is an integer equal to 0 or 1, and
y is an integer equal to 0 or 1.

The "spacer chain" denoted [SPAC] in the compound of formula (I) may be of any known type. Said spacer chain has the function of physically distancing the deoxyribonucleic acid from the surface of the solid substrate on which said compound can be immobilized and of allowing a relative mobility of the nucleic acid relative to the surface of the solid substrate on which it can be immobilized. The spacer chain limits or prevents steric hindrance due to the solid substrate and the nucleic acid being too close to one another, thereby impeding binding events between said nucleic acid and molecules of plasma protein that may be brought into contact with said nucleic acid.

In the compound of formula (I) the spacer chain is preferentially bonded to the 5' end or to the 3' end of the aptamer deoxyribonucleic acid.

Advantageously, the spacer chain is bonded both to one end of the aptamer and to the solid substrate. This construction with a spacer has the advantage of not directly immobilizing the aptamer on the solid substrate. Preferably, the spacer chain is a nonspecific oligonucleotide or polyethylene glycol (PEG). When the spacer chain consists of a nonspecific oligonucleotide, said oligonucleotide advantageously comprises at least 5 nucleotides in length, preferably between 5 and 15 nucleotides in length.

In the embodiments of a compound of formula (I) in which the spacer chain consists of a polyethylene glycol, said spacer chain encompasses a polyethylene glycol of PEG(C18) type, sold, for example, by the company Sigma Aldrich.

In order to immobilize the aptamer on the spacer chain, the deoxyribonucleic acid may be chemically modified with various chemical groups, such as groups which make it possible to immobilize said nucleic acid covalently, for instance thiols, amines or any other group capable of reacting with chemical groups present on the solid substrate.

In the compound of formula (I), the compound [FIX] consists of a compound chosen from (i) a compound capable of forming one or more covalent bond(s) with the solid substrate material and (ii) a compound capable of bonding specifically to the solid substrate by means of weak noncovalent bonds, including hydrogen bonds, electrostatic forces or Van der Waals forces.

The first type of compound [FIX] encompasses bifunctional coupling agents, such as glutaraldehyde, SIAB or else SMCC.

The compound SIAB, described by Hermanson G. T. (1996, Bioconjugate techniques, San Diego: Academic Press, pp 239-242), is the compound of formula (I) below:

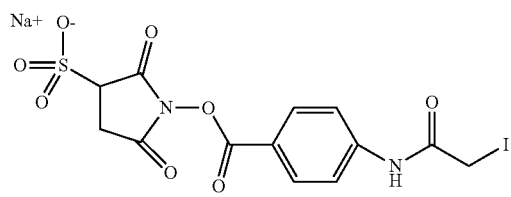

(I)

The compound SIAB comprises two reactive groups, respectively an iodoacetate group and a sulfo-NHS ester group, these groups reacting respectively with amino and sulfhydryl groups.

The compound SMCC, which is described by Samoszuk M. K. et al. (1989, Antibody, Immunoconjugates Radiopharm., 2(1): 37-46), is the compound of formula (II) below:

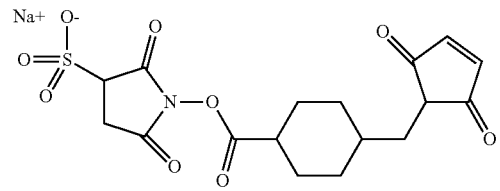

(II)

The compound SMCC comprises two reactive groups, respectively a sulfo-NHS ester group and a maleimide group, which react respectively with an amino group and a sulfhydryl group.

The second type of compound [FIX] encompasses biotin, which is capable of binding specifically in a noncovalent manner to avidin or streptavidin molecules present on the mobile substrate.

Nucleic aptamers capable of binding to various proteins involved in the blood coagulation pathway are already known in the prior art, including aptamers which bind von Willebrand factor (PCT application No. WO 2008/150495), aptamers which bind alpha-thrombin (European patent application No. EP 1 972 693) or thrombin (Zhao et al., 2008, Anal Chem, Vol. 80(19): 7586-7593), aptamers which bind factor IX/IXa (Subash et al., 2006, Thromb Haemost, vol. 95: 767-771; Howard et al., 2007, Atherioscl Thromb Vasc Biol, vol. 27: 722-727; PCT application No. WO 2002/096926; U.S. Pat. No. 7,312,325), and aptamers which bind factor X/Xa (PCT application No. WO 2002/096926; U.S. Pat. No. 7,312,325).

Nucleic aptamers which bind to human factor VII/VIIa have also been described in the prior art (Rusconi et al., 2000, Thromb Haemost, vol. 84(5): 841-848; Layzer et al., 2007, Spring, vol. 17: 1-11).

It is specified that none of the above aptamers, which consist principally, if not exclusively, of ribonucleotide aptamers, is described for the use thereof for purifying the target protein to which they bind.

As already mentioned, a specific advantage of the deoxyribonucleic aptamers concerns the ease with which they can be produced, compared with the difficulties in synthesizing RNA aptamers, and also their cost price, which is significantly lower than the cost price of an RNA aptamer.

A subject of the present invention is also an affinity chromatography device for purifying a plasma protein, comprising a container in which a suitable amount of an affinity substrate as defined in the present description is deposited.

Varied forms of containers for chromatography substrates are known in the prior art and are encompassed by the meaning of the term "container" above. The important characteristics of such a container encompass the presence of a means for feeding the affinity chromatography device with starting sample and of a means for output of the liquid after it has been brought into contact with the affinity substrate.

A subject of the present invention is also a method for immobilizing a plasma protein on a support, comprising a step during which a sample containing said plasma protein of interest is brought into contact with an affinity substrate as defined above.

The expression "sample containing a plasma protein" is intended to mean in general any type of liquid solution in which said plasma protein is in suspension or is solubilized. Specific embodiments of such a sample, in particular in relation to the purification method described hereinafter, will be subsequently defined in the present description.

The present invention also relates to a method for purifying a plasma protein, comprising the following steps:
a) bringing a sample containing a plasma protein into contact with an affinity substrate as defined in the present description, in order to form complexes between (i) the deoxyribonucleic aptamers immobilized on said affinity substrate and (ii) said plasma protein, and
b) releasing the protein from the complexes formed in step a), and
c) recovering said plasma protein in a purified form.

In some preferred embodiments, said sample contains a human plasma protein. Advantageously, in these embodiments, the sample containing a plasma protein of interest consists of a liquid sample which contains said protein of interest, including a liquid sample comprising said protein of interest and which is capable of also containing molecules of the homologous plasma protein of a nonhuman mammal. In some embodiments of the purification method above, said sample consists of a biological solution, such as a body fluid, a cell, ground cell material, a tissue, ground tissue material, an organ or a whole organism.

In some embodiments of the purification method above, said sample consists of a liquid biological solution originating from an animal, such as blood, a blood derivative, mammalian milk or a mammalian milk derivative. Said sample can consist of plasma, plasma cryoprecipitate, clarified milk, or derivatives thereof.

In particularly preferred embodiments of the purification method above, said sample originates from an animal that is transgenic for the human protein of interest. Advantageously, the solution is milk from a mammal or a derivative of milk from a mammal that is transgenic for said human protein of interest. For the purpose of the invention, the transgenic animals encompass (i) nonhuman mammals such as cows, goats, rabbits, pigs, monkeys, rats or mice, (ii) birds or else (iii) insects such as mosquitoes, flies or silkworms. In some preferred embodiments, the animal that is transgenic for the human protein of interest is a nonhuman transgenic mammal, entirely preferably a doe rabbit that is transgenic for said human protein of interest. Advantageously, the transgenic mammal produces said recombinant human protein of interest in its mammary glands, owing to the insertion into its genome of an expression cassette comprising a nucleic acid encoding said protein of interest, which is placed under the control of a specific promoter allowing the expression of the transgenic protein in the milk of said transgenic mammal.

A method for producing said human plasma protein in the milk of a transgenic animal can comprise the following steps: a DNA molecule comprising a gene encoding the protein of interest, said gene being under the control of a promoter of a protein naturally secreted in milk (such as the casein promoter, the beta-casein promoter, the lactalbumin promoter, the beta-lactoglobulin promoter or the WAP promoter), is integrated into an embryo of a nonhuman mammal. The embryo is then placed in a mammalian female of the same species. Once the mammal resulting from the embryo is sufficiently developed, lactation by the mammal is induced, and the milk is then collected. The milk then contains the recombinant human protein of interest.

An example of a method for preparing protein in the milk of a mammalian female other than a human being is given in document EP 0 527 063, the teaching of which can be reproduced for producing the protein of the invention. A plasmid containing the WAP (Whey Acidic Protein) promoter is produced by introducing a sequence comprising the promoter of the WAP gene, this plasmid being prepared in such a way as to be able to receive a foreign gene placed under the control of the WAP promoter. The plasmid containing the promoter and the gene encoding the protein of the invention is used to obtain transgenic doe rabbits by microinjection into the male pronucleus of embryos of doe rabbits. The embryos are then transferred into the oviduct of hormonally prepared females. The presence of the transgenes is revealed by the Southern technique using the DNA extracted from the young transgenic rabbits obtained. The concentrations in the milk of the animals are evaluated by means of specific radioimmunological assays.

Other documents describe methods for preparing proteins in the milk of a mammalian female other than a human being. Mention may be made, without being limited thereto, of the documents U.S. Pat. No. 7,045,676 (transgenic mouse) and EP 1 739 170 (production of von Willebrand factor in a transgenic mammal).

The purification method of the invention is also perfectly suitable for obtaining a purified plasma protein from a sample of human blood plasma, or from a fraction of human blood plasma, for example the cryoprecipitated fraction of human blood plasma.

In some embodiments of the purification method above, the target blood plasma protein is human.

In some embodiments of the purification method above, the sample comprises at least one nonhuman blood plasma protein.

In some embodiments of the purification method above, said human blood plasma protein is homologous to said nonhuman plasma protein.

In some embodiments of the purification method above, said human blood plasma protein is the homolog of said nonhuman plasma protein.

In some embodiments of the purification method above, the starting sample can consist of the crude material, either the sample of human blood plasma, or a fraction thereof, or the body fluid of a nonhuman mammal that is transgenic for the protein of interest, and which contains said protein of interest to be purified. The body fluids of a transgenic nonhuman mammal encompass the milk or a fraction of the milk, for example a defatted fraction of the milk or alternatively a casein-micelle-depleted fraction.

However, the above embodiment is not the preferred embodiment of the purification method of the invention, in particular owing to the risk of clogging of the affinity substrate by the numerous proteins present in the crude starting sample.

In preferred embodiments, said starting sample consists of a liquid solution containing the plasma protein of interest in suspension in said solution, said liquid solution consisting of an intermediate product generated during a multistep method for purifying a plasma protein.

By way of illustration, for a method for purifying a plasma protein from a body fluid of a nonhuman mammal that is transgenic for said protein, the starting sample may consist of an eluate of an ion exchange chromatography carried out using a filtrate of milk of said nonhuman transgenic mammal. This particular embodiment of a purification method according to the invention is illustrated in the examples.

In the same way, for a method for purifying the plasma protein of interest from human plasma, the starting sample may consist of a filtrate of a deep filtration step carried out on the cryoprecipitated fraction of a sample of human plasma.

Generally, the conditions for using the affinity substrate in order to carry out the purification method of the invention are very similar to the customary conditions for using a conventional chromatography substrate, for example of the immunoaffinity substrate type on which ligand antibodies are immobilized. Those skilled in the art may, for example, refer to the book by Bailon et al. (Pascal Bailon, George K. Ehrlich, Wen-Jian Fung and Wolfgang Berthold, An Overview of Affinity Chromatography, Humana Press, 2000).

However, as will be detailed in the subsequent description, the conditions of elution step c) of the method of the invention are very advantageous for purifying a plasma protein.

In step a), a suitable volume of the sample to be purified is brought into contact with the affinity substrate. Complexes are formed between (i) the nucleic aptamers immobilized on said affinity substrate and (ii) the plasma protein of interest contained in the sample to be purified.

It has been shown in the examples that the conditions for capturing factor VII are improved when a buffer containing a low concentration of $MgCl_2$ or even a buffer free of $MgCl_2$ is used in step a).

The expression "buffer with a low concentration of $MgCl_2$" is intended to mean, according to the invention, a buffer of which the final $MgCl_2$ concentration is less than 1 mM.

A buffer of which the $MgCl_2$ concentration is less than 1 mM encompasses buffers of which the $MgCl_2$ concentration is less than 0.5 mM, 0.1 mM, 0.05 mM and 0.01 mM, advantageously equal to 0 mM.

In one particular embodiment, the method comprises a step a') of washing the affinity substrate with a washing buffer. Advantageously, the method comprises a step a') of washing the affinity substrate while increasing the ionic strength, i.e. with a washing buffer of which the ionic strength is increased compared with the ionic strength of step a). Advantageously, the ionic strength of the washing buffer is increased by 2- to 500-fold compared with the ionic strength of step a). Advantageously, the ionic strength of the washing buffer is increased by 100- to 500-fold, preferably by 200- to 500-fold, compared with the ionic strength of step a).

It has been shown in the examples that the use, in step a'), of a washing buffer having a high ionic strength, in particular a high NaCl concentration, makes it possible to effectively eliminate the substances bound nonspecifically to the affinity substrate without simultaneously affecting, in a detectable manner, the binding of factor VII to the affinity substrate.

In step a'), a washing buffer having a final NaCl concentration of at least 1 M is thus preferably used.

According to the invention, a washing buffer having a final NaCl concentration of at least 1 M encompasses washing buffers having a final NaCl concentration of at least 1.5 M, 2 M, 2.5 M or at least 3 M.

Preferably, a washing buffer used in step a') of the method has a final NaCl concentration of at most 3.5 M. Advantageously, a washing buffer used in step a') of the method has a final NaCl concentration of between 1.5 and 3.5, preferably between 2 and 3.5, preferably between 2.5 and 3.5, preferably between 3 and 3.5.

It has also been shown in the examples that the use, in step a'), of a washing buffer having a high hydrophobicity, in particular a high propylene glycol concentration, makes it possible to effectively eliminate the substances bound nonspecifically to the affinity substrate without simultaneously affecting, in a detectable manner, the binding of factor VII to the affinity substrate.

In step a'), a washing buffer having a final propylene glycol content of at least 20% (v/v) is thus preferably used.

According to the invention, a washing buffer having a final propylene glycol content of at least 20% encompasses washing buffers having a final propylene glycol content of at least 25%, 30%, 35%, 40%, 45%, 50%, 55%, or at least 60% by volume, relative to the total volume of the washing buffer.

Preferably, a washing buffer used in step a') of the method has a final propylene glycol content of at most 50%. Advantageously, a washing buffer used in step a') of the method has a final propylene glycol content of between 20% and 50%, preferably between 30% and 50%.

According to one particular embodiment, the washing buffer used in step a') contains both NaCl and propylene glycol as described above.

Step b) consists of a step of eluting the molecules of the plasma protein of interest having formed complexes with the nucleic aptamers during step a).

As is illustrated in the examples, a specific advantage of the purification method above is the possibility of carrying out the elution step by bringing the complexes formed between (i) the nucleic aptamers immobilized on said affinity substrate and (ii) said plasma protein into contact with a divalent-ion-chelating agent, such as EDTA.

This technical advantage, which is made possible by virtue of the characteristics of the affinity substrate of the invention, allows the elution of the plasma protein without requiring any recourse to the use of drastic elution conditions, capable of at least partially denaturing the plasma protein of interest. Said drastic conditions which are avoided encompass the use of an acidic pH for the elution step, which is commonly implemented for methods for purifying proteins on affinity substrates that are known, and most particularly on affinity substrates comprising immobilized antibodies.

Thus, in some embodiments of the purification method above, step b) is carried out by bringing the affinity substrate into contact with an elution buffer containing a divalent-ion-chelating agent, preferably EDTA.

By way of illustration, the elution buffer may contain a final EDTA concentration of at least 1 mM and of at most 30 mM.

The expression "at least 1 mM" encompasses at least 2, 3, 4, 5, 6, 7, 8, 9 or 10 mM.

The expression "at most 30 mM" encompasses at most 29, 28, 27, 26, 25, 24, 23, 22, 21, 20, 19, 18, 17, 16, 15, 14, 13, 12 or 11 mM.

In step c), the purified plasma protein of interest is recovered by collecting the eluate liquid obtained at the end of step b).

At the end of step c), a purified liquid composition of the plasma protein of interest is obtained. Said purified liquid composition can then be treated appropriately, according to any known technique for conditioning and storing proteins, including by direct bottling or bottling after dilution with a suitable solution, or else by freeze-drying, preferentially under sterile and apyrogenic conditions, and then storage under appropriate conditions, at ambient temperature, at −4° C. or else at a low temperature, depending on the type of conditioning selected.

As has already been mentioned previously in the present description, the affinity substrate of the invention can, with the successive cycles of use for purifying a plasma protein of interest, experience a reduction in its absorption capacity, for example owing to the fact that elution step c) does not make it possible to systematically release all of the molecules of plasma protein, thereby reducing the number of free aptamer sites for the subsequent purification cycles.

As for all known chromatography substrates, it is therefore necessary, at appropriate times, to carry out a step of regenerating the affinity substrate, in order to release all of the molecules of plasma protein from said substrate, and to eliminate any substance that may be bound to the solid material of the affinity substrate, generally by nonspecific binding.

Thus, in some embodiments, the purification method of the invention comprises an additional step d) of regenerating the affinity substrate by bringing said affinity substrate into contact with a regenerating solution.

Varied buffers for regenerating chromatography substrates, in particular affinity chromatography substrates, are well known by those skilled in the art, and can be used in step d) of the method. Those skilled in the art may refer, for example, to the book by Mohr et al. (Affinity Chromatography: Practical and Theoretical Aspects, Peter Mohr, Klaus Pommerening, Edition: illustrated, CRC Press, 1985).

By way of illustration, step d) of regenerating the affinity substrate can be carried out by bringing said substrate into contact with a 50 mM Tris, 50% ethylene glycol buffer solution as is illustrated in the examples.

As is illustrated in the examples, the purification method above makes it possible to obtain a plasma protein at a very high degree of purity, optionally at a degree of purity of greater than 99.95% by weight, relative to the total weight of the proteins contained in the purified final product.

Another advantage of the purification method above, in particular in the embodiments in which the starting sample consists of a sample comprising the human plasma protein of interest in recombinant form as a mixture with proteins naturally produced by the nonhuman transgenic mammal, is that the final composition comprising the recombinant human protein of interest at a high degree of purity is substantially free of proteins originating from said transgenic mammal, and in particular substantially free of proteins of said mammal, which are homologs of said recombinant human protein.

By way of illustration, it has been shown in the examples that recombinant human factor VII produced in the milk of a transgenic rabbit, then purified with the purification method defined in the present description, comprises less than 1.5% by weight of the proteins of said transgenic mammal, relative to the weight of said proteins initially contained in the starting sample. In the same implementation of the purification method according to the invention, 85% by weight of the recombinant human factor VII present in the starting sample was contained in the final product at a high degree of purity with respect to recombinant human factor VII, greater than 99.95% of the weight of the proteins present.

A subject of the present invention is also a purified composition of a recombinant human plasma protein comprising at least 99.9% by weight of said recombinant human protein and which is substantially free of nonhuman proteins.

The present invention also relates to a purified composition of a recombinant human plasma protein comprising at least 99.9% by weight of said recombinant human protein and at most 0.01% by weight of nonhuman proteins, the percentages by weight being expressed relative to the total weight of proteins of said purified composition.

In the purified composition above, "at least 99.9%" encompasses at least 99.91%, 99.92%, 99.93%, 99.94%, 99.95%, 99.96%, 99.97%, 99.98% and 99.99%.

In the purified composition above, "at most 0.01%" encompasses at most 0.09%, 0.08%, 0.07%, 0.06%, 0.05%, 0.04%, 0.03%, 0.02% and 0.01%.

The present invention also relates to a purified composition as defined above, that can be used as a medicament.

The invention further relates to a pharmaceutical composition comprising a purified composition of a recombinant human plasma protein as defined above, in combination with one or more pharmaceutically acceptable excipients.

The invention also relates to a purified composition as defined above, for treating coagulation disorders.

The invention also relates to the use of a purified composition as defined above, for producing a medicament for treating coagulation disorders.

Specific embodiments of aptamers which bind specifically to a coagulation protein, which can be advantageously used according to the invention, are described below.

Specific Embodiments of Aptamers that can be Used According to the Invention

The applicant has constructed a family of nucleic aptamers which bind specifically to blood plasma proteins, and in particular to human factor VII/VIIa, for which it has been able to show the existence of relationships between (i) the common structural characteristics and (ii) the common functional characteristic(s).

From a structural point of view, the family of nucleic acids, or nucleic aptamers, which bind specifically to human factor VII/VIIa and which can be used according to the invention comprises at least 15 consecutive nucleotides of a polynucleotide having at least 40% nucleotide identity with the nucleic acid of formula (I) below:

5'-[SEQ ID NO: 1]x-[SEQ ID No. X]-[SEQ ID NO: 2]y-3'  (I), in which:
"SEQ ID NO: X" consists of a nucleic acid chosen from the group consisting of the nucleic acids of sequences SEQ ID NO: 3 to SEQ ID NO: 85 and SEQ ID NO: 87 to SEQ ID NO: 100.
"x" is an integer equal to 0 or 1, and
"y" is an integer equal to 0 or 1.

In some embodiments, the acid of sequence SEQ ID NO: X has a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides.

In other embodiments, the nucleic acid of sequence SEQ ID NO: X has a length of 43, 44, 45, 46, 47, 48 or 49 nucleotides.

In some other preferred embodiments, the nucleic acid of sequence has a sequence length of 43, 44, or 45 nucleotides.

As already mentioned previously, the nucleic acid of formula (I) is at least 15 nucleotides in length.

In some embodiments, the nucleic acid of formula (I) is at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 or 81 nucleotides in length, which encompasses the nucleic acids having exactly each of the specified lengths.

In some embodiments of the method for obtaining the aptamers of formula (I), the successive selection cycles carried out in order to construct the family of nucleic acids of interest which bind specifically to blood plasma proteins have resulted in isolating and characterizing, at each successive selection step, sets and subsets of nucleic aptamers comprising, at their 5' and 3' ends respectively, the sequences SEQ ID NO: 1 and SEQ ID NO: 2, structurally framing a variable sequence SEQ ID NO: X. In the main family of nucleic aptamers of the invention, all the variable sequences SEQ ID NO: X have, between them, a nucleotide sequence identity of at least 40%. This means that, for the sequence SEQ ID NO: X, the structural constraints, for retaining the property of binding to blood plasma proteins, are much less than the structural constraints for the sequences located, respectively, at the 5' and 3' ends of these nucleic aptamers.

When the integer "x" is equal to 0 and the integer "y" is equal to 1, the nucleic aptamers of the invention encompass the nucleic acids comprising at least 15 consecutive nucleotides of a polynucleotide having at least 40% nucleotide identity with the nucleic acid of formula (1-1) below:

5'-[SEQ ID NO: X]-[SEQ ID NO: 2]-3'     (I-1).

When the integer "x" is equal to 1 and the integer "y" is equal to 0, the nucleic aptamers of the invention encompass the nucleic acids comprising at least 15 the nucleic acid of formula (1-2) below:

5'-[SEQ ID NO: 1]-[SEQ ID NO: X]-3'     (I-2).

When the integer "x" is equal to 0 and the integer "y" is equal to 0, the nucleic aptamers of the invention encompass the nucleic acids comprising at least 15 consecutive nucleotides of a polynucleotide having at least 40% nucleotide identity with the nucleic acid of formula (1-3) below:

5'-[SEQ ID NO: X]-3'     (I-3).

The nucleic aptamers above therefore encompass the nucleic acids comprising at least 15 consecutive nucleotides of a polynucleotide having at least 40% nucleotide identity with a nucleic acid chosen from the group consisting of the nucleic acids of sequences SEQ ID NO: 3 to SEQ ID NO: 85 and SEQ ID NO: 87 to SEQ ID NO: 100.

Generally, a first polynucleotide having at least 40% nucleotide identity with a second polynucleotide or a nucleic acid has at least 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 100% nucleotide identity with said second polynucleotide or nucleic acid.

In some embodiments of a nucleic acid of the invention comprising the sequence SEQ ID NO: X, said sequence SEQ ID NO: X is chosen from the group consisting of the nucleic acids having at least 15 consecutive nucleotides of a sequence having at least 40% nucleotide identity with at least one of the sequences SEQ ID NO: 3 to SEQ ID NO: 85 and SEQ ID NO: 87 to SEQ ID NO: 100.

In some embodiments of a nucleic acid of the invention comprising the sequence SEQ ID NO: X, said sequence SEQ ID NO: X is chosen from the group consisting of the nucleic acids having at least 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 100% nucleotide identity with at least one of the sequences SEQ ID NO: 3 to SEQ ID NO: 85 and SEQ ID NO: 87 to SEQ ID NO: 100.

It results from the aforementioned that the present invention encompasses a family of single-stranded nucleic acids having at least 15 consecutive nucleotides of the series of formula (I) defined above.

The "percentage identity" between two nucleic acid sequences, for the purpose of the present invention, is determined by comparing the two sequences optimally aligned, through a window of comparison.

The part of the nucleotide sequence in the window of comparison can thus comprise additions or deletions (for example "gaps") compared with the reference sequence (which does not comprise these additions or these deletions) in such a way as to obtain an optimum alignment between the two sequences.

The percentage identity is calculated by determining the number of positions at which an identical nucleic base is observed for the two compared sequences, and then by dividing the number of positions at which there is identity between the two nucleic bases by the total number of positions in the window of comparison, and then by multiplying the result by one hundred in order to obtain the percentage nucleotide identity of the two sequences with respect to one another.

The optimal alignment of the sequences for the comparison can be carried out by computer using known algorithms. Entirely preferably, the percentage sequence identity is determined by means of the CLUSTAL W software (version 1.82), the parameters being fixed as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAP DISTANCES="hide".

The present invention is also illustrated by the following examples.

EXAMPLES

Example 1

Preparation of an Affinity Substrate

The affinity substrate was prepared from a solid substrate material consisting of a matrix onto which streptavidin (streptavidin-agarose—Novagen®) was grafted.

A volume of 1 ml of gel was placed in a container consisting of a column (i.d. 11 mm). The gel was washed with purified water, in order to remove the storage solvent. The characteristics of the gel are:

Biotin adsorption capacity: ≥85 nanomol/ml of gel

Functional test: capture >99% of biotinylated thrombin over the course of 30 minutes at AT Other tests: Protease-free, endo/exonuclease-free, RNase-free Preservative: 100 mM sodium phosphate pH 7.5+NaN$_3$ 0.02

The outlet of the packed column (gel bed height=1 cm) is connected to an absorbance detector equipped with a UV filter at 254 nm and a recording device.

The biotinylated anti-human FVII nucleic aptamers of sequence SEQ ID NO: 86 are solubilized in purified water at a final concentration of 0.5 mg/0.187 ml, i.e. a final molar concentration of 0.1 mM. The solution of nucleic aptamers was activated at 95° C. according to the standard cycle, for the immobilization of the aptamers on the solid substrate material.

The solution of nucleic aptamers was prediluted with 4.8 ml of purified water and then 1.5 ml of Me$^{++}$ buffer (5× concentrated).

The absorbance detector is adjusted to 1 AUFS (absorbance unit full scale) and the OD at 254 nm of this solution is recorded at 0.575 AU$_{254}$.

The solution of biotinylated nucleic aptamers is injected onto the prepacked streptavidin-agarose gel and recirculated with a peristaltic pump at a flow rate of 2.5 ml/minute, i.e. a contact time on the gel of 24 seconds (inlet/outlet I/O). Under these conditions, the OD at 254 nm stabilizes rapidly at 0.05 AU$_{254}$, i.e. a theoretical coupling value of 91%, i.e. 0.455 mg of nucleic aptamers per milliliter of gel.

Washing with a 10 mM CaCl$_2$+4 mM MgCl$_2$ buffer and then in 2 M NaCl is carried out in order to eliminate the nucleic aptamers which are not bound specifically to the streptavidin molecules grafted onto the solid substrate material.

Example 2

Method for Purifying Recombinant Human Factor VII

The aptamer affinity substrates were tested using a purified preparation of FVII/FVIIa prepared according to the technique described in PCT application No. WO2008/099077.

Preparation of the Sample to be Purified

The starting biological material is transgenic rabbit milk containing recombinant human FVII. The expression cassette comprises the human FVII transgene placed under the control of the β-casein gene promoter.

Briefly, 140 milliliters of milk were collected from 2 rabbits in first lactation between day 4 and day 12 after having given birth.

The average titer of amidolytic FVII (biologically activatable FVII) in the milk collected is 928 IU/ml. The milks are stored at a temperature of −80° C.

For the test, the rabbit milks are thawed in a water bath at a temperature of 37° C., and are then diluted with a sodium citrate solution to give a final citrate concentration of 62 g/l at a pH of 7.5.

The treatment with sodium citrate makes it possible to destabilize the phosphocalcic casein micelles.

The lipid-rich protein solution of milk is then clarified over a sequence of filters, respectively (i) depth filter of 15 to 0.5 μm porosity threshold and then (ii) membrane filter at 0.2 μm.

A volume of 360 ml of filtered solution having an FVII titer of 198 IU/ml, i.e. 36 mg of transgenic FVII, is prepurified on an MEP-HyperCel® chromatography gel (Pall BioSepra) having a volume of 16 ml. This capture gel makes it possible to eliminate 95% of the milk proteins, including the majority of caseins, while at the same time retaining 60% of the initial amount of FVII.

An amount of 17.5 mg of low-purity FVII (~5%) obtained at the end of the above step is purified by ion exchange chromatography using a Q-Sepharose® XL gel (GE Healthcare) having a volume of 20 ml, the human FVII being eluted with a volume of 78 ml of buffer comprising 5 mM of calcium chloride. The concentration of amidolytic FVII is 337 IU/ml, i.e. 0.17 mg of FVII/ml, and the concentration of total proteins is estimated at 0.18 mg/ml by measurement of OD at 280 nm and $\epsilon^{1\%}$=13, i.e. an FVII purity of 94%.

The residual proteins originating from the rabbit milk are difficult to separate from the FVII at this stage, either because there are structural homologies, such as GLA-domain or EGF-domain proteins, or else because there are physicochemical homologies (similar ionic charge and/or molecular size). Conventional techniques allow an improvement in purity up to 99.95% by means of orthogonal techniques (combination of separation on hydroxyapatite gel and by size exclusion chromatography). However, for repeated injection in humans, the load with respect to exogenous proteins accepted for genetic recombination proteins must not exceed 50 ppm, i.e. a purity >99.995%. Such a purity appears to be attainable only after purification on an affinity matrix.

Step of Purifying Recombinant Human FVII on the Affinity Substrate of the Invention A volume of 6 ml of the solution of purified human FVII (1.1 mg of FVII) obtained at the end of the preceding step is used for the step for purifying the recombinant human FVII at a high level of purity with the affinity substrate of the invention.

The FVII solution obtained in the preceding step, preadjusted to 4 mM MgCl$_2$ and 10 mM CaCl$_2$ and pH 7.5, is injected onto the aptamer-agarose gel (affinity substrate) with a peristaltic pump at a flow rate of 0.1 ml/minute, i.e. a contact time with the affinity substrate of 10 minutes (I/O).

After injection, the gel is washed in 50 mM tris+NaCl 50 mM+4 mM MgCl$_2$+10 mM CaCl$_2$ buffer at pH 7.5.

A nonadsorbed volume of 10 ml of solution is collected.

The FVII is eluted with a 50 mM tris+EDTA 10 mM buffer at pH 7.5. The collection of the elution peak is carried out according to the OD profile.

According to the molar calculations, the amount of nucleic aptamers immobilized in the affinity substrate is 17 nanomol, which corresponds, for a mole-for-mole interaction with the FVII molecules, to an absolute capacity of the affinity substrate of 0.9 mg of FVII.

FIG. 1 illustrates a chromatography profile of the recombinant human FVII produced in the rabbit milk, with continuous monitoring of the absorbance (OD) values at 254 nanometers.

In FIG. 1, the inflexion (2) of the absorption curve, after the moment of the injection (1), illustrates the beginning of the saturation of the affinity substrate with the recombinant human FVII. At time (3), the injection of recombinant human FVII is stopped. To illustrate the linear scale of the times in FIG. 1, it is indicated that the duration between the injection start time (1) and the injection end time (3) is 10 minutes. The affinity substrate continues to be saturated with the coagulation protein of interest: complexes between (i) the anti-FVII nucleic aptamers of the affinity substrate and (ii) the molecules of recombinant human FVII initially contained in the composition to be purified have been formed. After the composition to be purified has been passed over the column, a step of washing (6) the column with the washing buffer specified above is carried out. The elution step is then carried out, by injection, at time (4), of the buffer solution comprising a final EDTA concentration of 10 mM. The absorption peak illustrates the release of the recombinant human FVII from the nucleic aptamer/recombinant FVII complexes. It is noted that the molecules of recombinant human FVII are released rapidly and therefore in a small volume. Consequently, by virtue of the affinity substrate of the invention, an elution solution with a high concentration of recombinant human FVII protein is obtained. At time (5), a step of regenerating the affinity substrate is carried out with a 50 mM tris buffer. The absorbance peak visible at (7) corresponds to the substances released from the affinity substrate owing to the regeneration step.

Dynamic Binding Capacity of the Affinity Substrate

Table 1 below gives the results of the test, which show a dynamic binding capacity of 0.45 to 0.49 mg/ml of the affinity matrices, i.e. 50 to 55% of bioavailable ligands.

In EDTA, a dynamic elution of approximately 75% is calculated.

TABLE 1 recombinant human FVII and total protein results of the aptamer-agarose matrix tests:

|  | Recombinant FVII |  | Proteins (total mg) |  | DBC (mg/ml) | DE (%) |
|---|---|---|---|---|---|---|
| Start | 2228 | 100% | 1.42 | 100% |  |  |
| Final |  |  |  |  |  |  |
| Nonadsorbed | 924 | 41% | 0.57 | 40% |  |  |
| Eluate | 971 | 44% | 0.61 | 43% | 0.49 | 74% |
| Results |  | 85% |  | 83% |  |  |
| by weight |  |  |  |  |  |  |

Start: starting sample
Final: fraction composition
DBC: dynamic binding capacity
DE: dynamic elution; which represents the ratio between the eluted recombinant FVII and the adsorbed recombinant FVII, expressed as a percentage Specific Separation Capacity of the Affinity Substrate The affinity substrates were evaluated in terms of specificity by means of an ELISA assay specific for rabbit milk proteins.

The results are represented in table 2 below.

TABLE 2 affinity substrate specificity results:

|  | Recombinant FVII (total mg) |  | Rabbit milk proteins (RMP) |  | RMP (ppm) | % FVII purity |
|---|---|---|---|---|---|---|
| Start | 1.11 | 100% | 16992 | 100% | 16782 | 98.32% |
| Final |  |  |  |  |  |  |
| Nonadsorbed | 0.46 | 41% | 14590 | 40% | 34738 | 96.53% |
| Eluate | 0.49 | 44% | 217 | 43% | 492 | 99.95% |
| Results |  | 85% |  | 83% |  |  |
| by weight |  |  |  |  |  |  |

The results in table 2 above show that an average of 2 $\log_{10}$ of elimination by the aptamers-agarose is obtained, taking the purity of the transgenic human FVII from 98.3% to 99.95%. This shows a good specificity of the aptamers with respect to human FVII and very few interactions with the residual rabbit milk proteins.

An improvement is possible by means of intermediate washes, before elution, with solutions such as 2M NaCl and/or propylene glycol or ethylene glycol at 50% if, under these conditions, the FVII is not eluted.

The results of example 2 illustrate the excellent characteristics of the affinity substrates on aptamer-agarose gel (Apta-2) with a dynamic binding capacity of at least 1 mg of FVII per mg of ligand with an elution yield of at least 75%. The specificity is also well established with a clear improvement in purity (~99.95%), with an elimination of 2 $\log_{10}$ of the residual rabbit milk proteins RMP. The final level comes to approximately 500 ppm over these 2 nonoptimized tests.

Example 3

Method for Purifying Human Plasma Factor IX

A. Materials and Methods

A.1. Affinity Chromatography Substrate

Mapt-1 affinity gel material, without spacer, theoretical ligand density 0.46 mg/ml: volume 1 ml.

The aptamer is directly bonded to the chromatography substrate material by means of a chemical coupling reaction.

The aptamer used is the aptamer of sequence SEQ ID NO: 101.

A.2. Starting Product

The starting product consists of a composition enriched in factor IX derived from human plasma, which is sold by LFB under the name Betafact®.

Starting material injected: Betafact MPVP (plasma FIX at 60% purity), load of 200 IU (i.e. 800 µg) of factor IX per ml of gel, contact time 10 minutes.

A.3. Purification Protocol

Gel equilibration: 0.050 M Tris-HCl, 0.010 M $CaCl_2$, pH 7.5,
Elution: 0.020 M Tris-HCl, 0.010 M EDTA, pH 7.5,
Regeneration: 0.020 M Tris-HCl, 1 M NaCl, 50% propylene glycol, pH 7.5.

The protein peaks are detected by measuring the absorbance value at the wavelength of 280 nanometers.

A.4. Protocol for Analysis by Electrophoresis on SDS Page Gel 10-well NOVEX gels (Invitrogen), 4-12%, Bis-Tris; MES running buffer, migration at 200 V for 50 min. CBB (G250) or $AgNO_3$ (GE kit) staining.

B. Results

Figure 2:
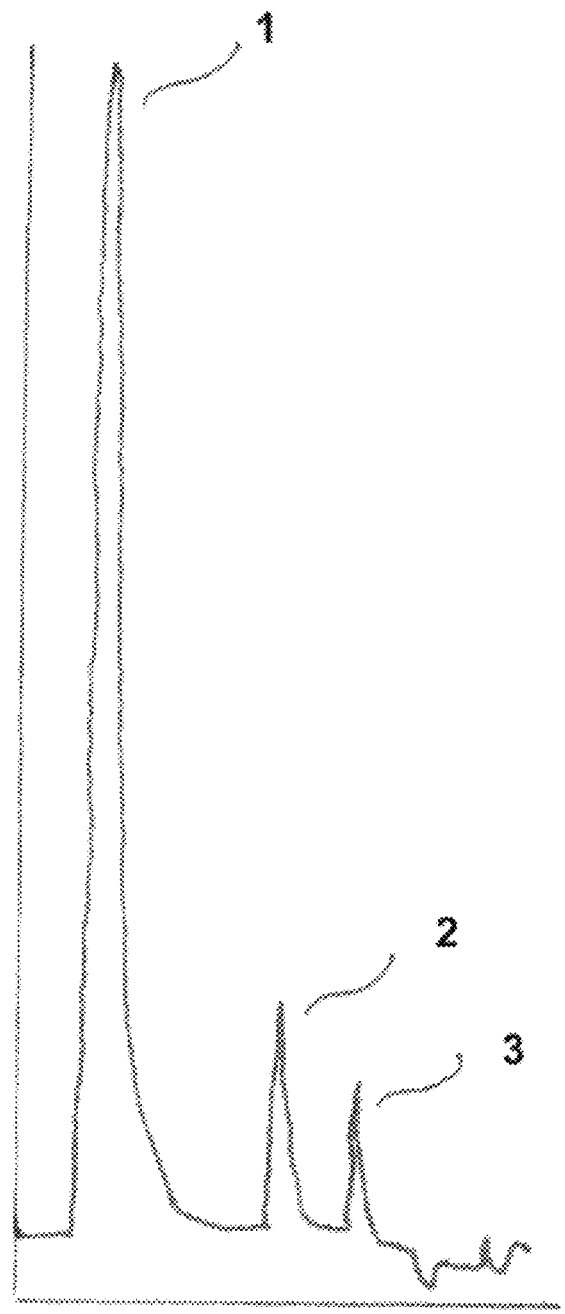
FIG. 2 represents the curve of the values of the measurement of absorbance at 280 nm as a function of time.
Figure 3:
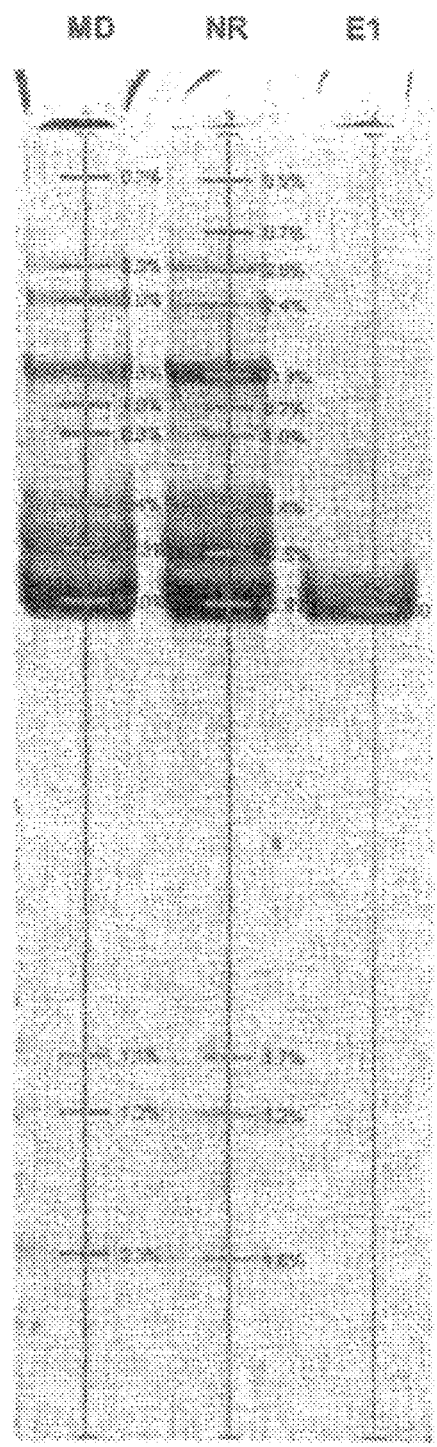
FIG. 3 is an image of an SDS PAGE electrophoresis gel with coomassie blue staining enabling relative quantification of the bands. From the left to the right of the gel in FIG. 3, the lanes represent the results of migration of the following starting products:
  lane "MD": the starting composition Betafact®,
  lane "NR": the nonretained fraction corresponding to peak No. 1 of the chromatographic profile of FIG. 2,
  lane "E1": the elution fraction corresponding to peak No. 2 of the chromatographic profile of FIG. 2.

The results are illustrated in FIGS. 2 and 3.

FIG. 2 represents the curve of the values of the measurement of absorbance at 280 nm as a function of time. In FIG. 2, peak No. 1 corresponds to the fraction of the starting product which was not retained on the column. Peak No. 2 corresponds to the elution fraction. Peak No. 3 corresponds to the fraction desorbed from the substrate by carrying out the regeneration step.

FIG. 3 is an image of an SDS PAGE electrophoresis gel. From left to right of the gel in FIG. 3, the lanes represent the results of migration of the following starting products:

lane "MD": the Betafact® starting composition,
lane "NR": the nonretained fraction corresponding to peak No. 1 of the chromatographic profile of FIG. 2,
lane "E1": the elution fraction corresponding to peak No. 2 of the chromatographic profile of FIG. 2.

TABLE 3

| Stage | % FIX |
|---|---|
| Starting product | 51% |
| Nonretained | 44% |
| Eluate | 100% |

Table 3 recapitulates the percentages of purity of the FIX obtained by integration of the electrophoretic profile in the various fractions. The % FIX is calculated according to a procedure well known to those skilled in the art, by quantitative integration of the densities of the electrophoretic bands of the gel stained with CBB (numerical data corresponding to FIG. 3). The quantitative integration of the densities of the electrophoretic bands can be obtained by scanning the gel with a suitable scanner.

The results represented in FIG. 3 and table 3 confirm those of FIG. 2. These results illustrate that the chromatography substrate on which the aptamer is immobilized allows the specific purification of human factor IX from a complex medium such as a plasma fraction enriched in factor IX.

It can be concluded that the eluate exhibits a good electrophoretic purity and is characterized by the fact that the functionality of the FIX is maintained. This experiment shows the capacity of the aptamer of sequence SEQ ID NO: 101 directly coupled to the chromatographic substrate, and therefore in the absence of a spacer chain, to bind and to purify FIX in a complex medium containing plasma impurities.

Example 4

Method for Purifying Recombinant Factor IX Contained in an Extract of Transgenic Sow's Milk A. Materials and Methods A.1. Affinity Chromatography Substrate Affinity gel material on which the Mapt-1 aptamer is immobilized by direct coupling without a spacer chain. Theoretical ligand density 0.46 mg/ml: volume 1 ml.

The aptamer is directly bonded to the chromatography substrate material by means of a chemical coupling reaction.

The aptamer used is the Mapt 1 aptamer of sequence SEQ ID NO: 101.

A.2. Starting Product

The starting product consists of a transgenic sows' milk clarified and prepurified on MEP HyperCel: 1.8% purity. Sample dialyzed against the buffer for adsorption/equilibration of the resin in order to remove the sodium citrate. Load of 302 IU (i.e. 1200 μg) of factor IX per ml.

A.3. Purification Protocol

Gel equilibration: 0.050 M Tris-HCl, 0.010 M $CaCl_2$, pH 7.5,
Elution: 0.020 M Tris-HCl, 0.010 M EDTA, pH 7.5,
Regeneration: 0.020 M Tris-HCl, 1 M NaCl, 50% propylene glycol, pH 7.5.

The sample is injected with a flow rate of 0.1 ml/min for 10 min, the gel is then washed for 5 min at 0.5 ml/min. The elution and the regeneration are carried out by injection of 2 ml of each of the buffers with a flow rate of 0.5 ml/min.

The protein peaks are detected by measuring the value of absorbance at the wavelength of 280 nanometers.

A.4. Protocol for Analysis by SDS Page Gel Electrophoresis 10-well NOVEX gels (Invitrogen), 4-12%, Bis-Tris; MES running buffer, migration at 200V for 50 min. CBB (G250) or $AgNO_3$ (GE kit) staining.

A.5. Protocol for Measuring the Specific Activity with Respect to Factor IX

The measurement of the amount of FIX (antigen measurement) was carried out with the Serachrom 0943 FIX Ag kit (Stago) according to the supplier's recommendations. The measurement of the enzymatic activity of the FIX was carried out by means of a chromogenic test with the Biophen FIX kit, ref. 221802 (Hyphen BioMed) according to the supplier's recommendations.

The specific activity is calculated according to the following ratio:
Enzymatic activity of the FIX/amount of FIX.

B. Results

Figure 4:
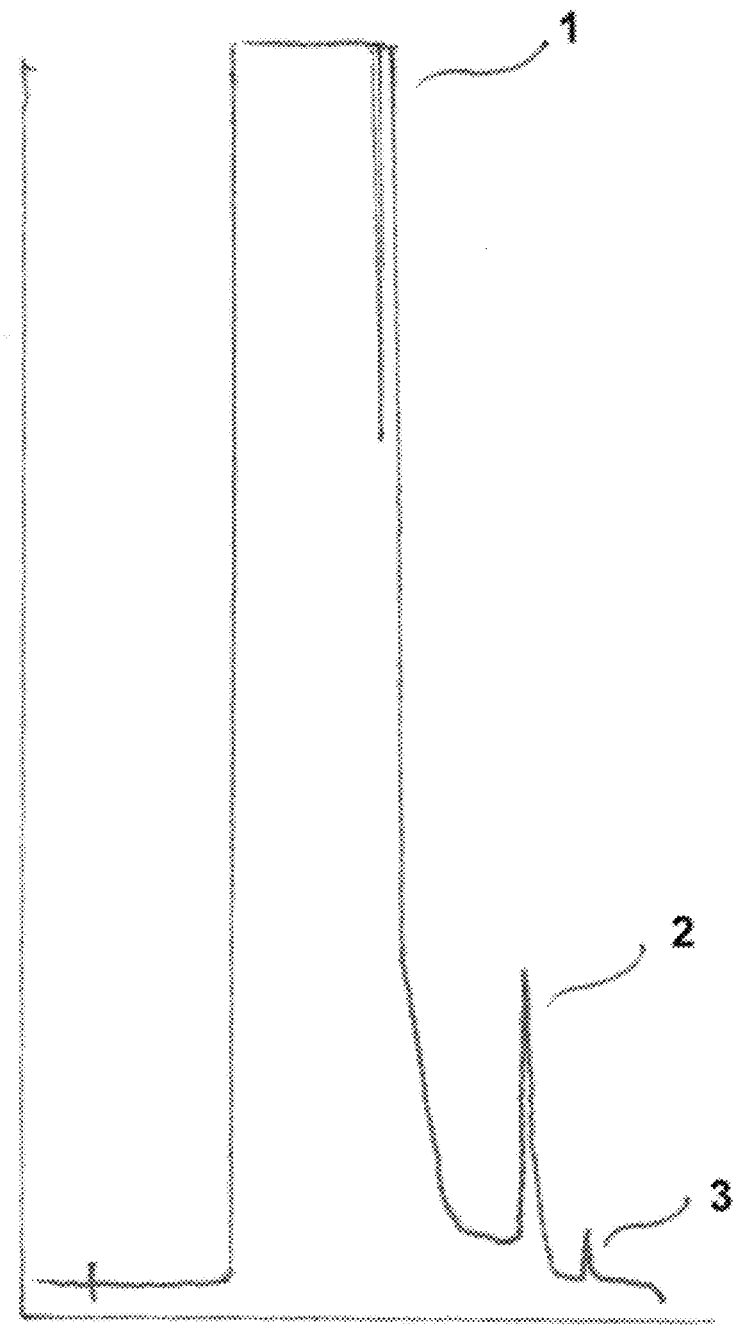
FIG. 4 represents the curve of the values of the measurement of absorbance at 280 nm as a function of time.
Figure 5:
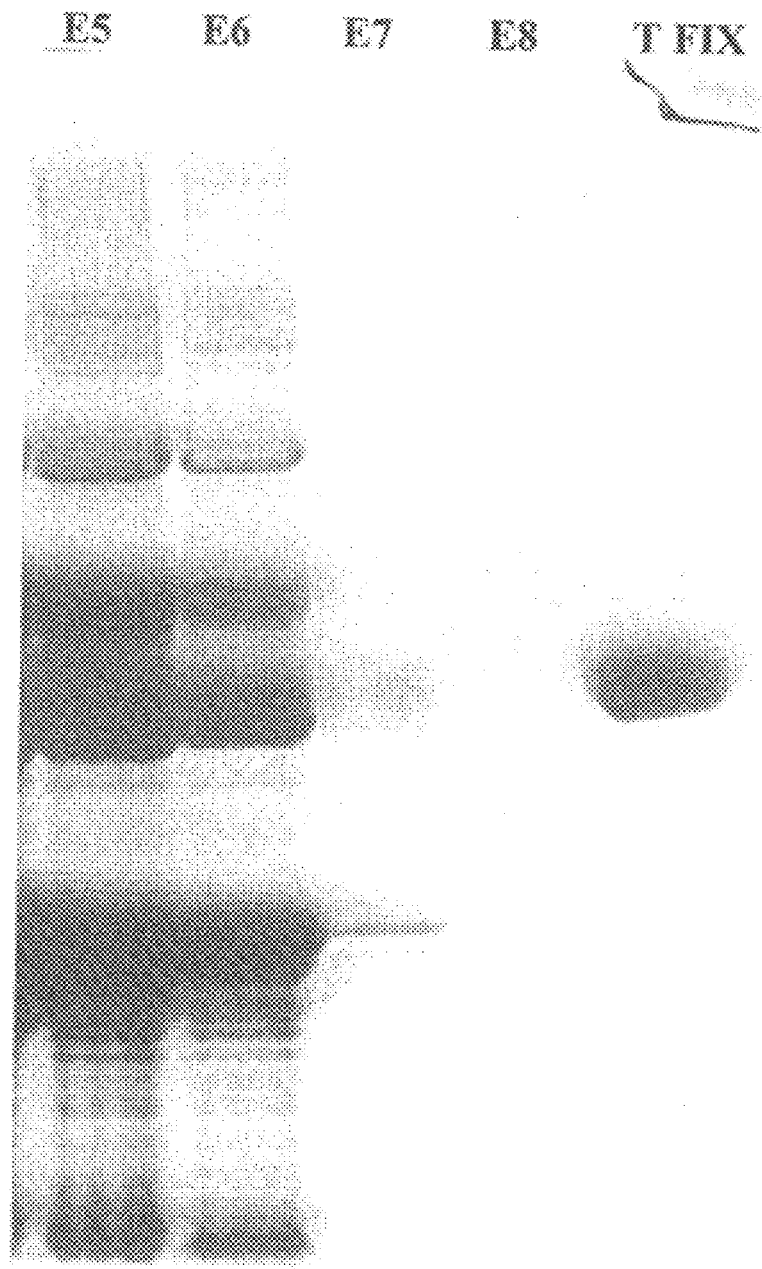
FIG. 5 is an image of an SDS PAGE electrophoresis gel. From the left to the right of the gel in FIG. 5, the lanes represent the results of migration of the following starting products:
  lane "E5": the starting composition of transgenic sow's milk containing transgenic human factor IX prepurified by means of an MEP HyperCel chromatographic step,
  lane "E6": the nonretained fraction corresponding to peak No. 1 of the chromatographic profile of FIG. 4,
  lane "E7": the elution fraction corresponding to peak No. 2 of the chromatographic profile of FIG. 4,
  lane "E8": the regeneration fraction corresponds to peak No. 3 of the chromatographic profile of FIG. 4,
  lane "T FIX": purified human plasma factor IX control.

The results are illustrated in FIGS. 4 and 5.
FIG. 4 represents the curve of the values of the measurement of absorbance at 280 nm as a function of time. In FIG. 4, peak No. 1 corresponds to the fraction of the starting product which was not retained on the column. Peak No. 2 corresponds to the elution fraction. Peak No. 3 corresponds to the fraction desorbed from the substrate by carrying out the regeneration step.

The results in FIG. 4 show that the elution peak is very narrow, which illustrates the very high specificity for human factor IX of the chromatography substrate on which the aptamer is immobilized.

FIG. 5 is an image of an SDS PAGE electrophoresis gel. From left to right of the gel in FIG. 5, the lanes represent the results of migration of the following starting products:
lane "E5": the starting composition of transgenic sow's milk containing transgenic human factor IX prepurified by an MEP HyperCel chromatographic step,
lane "E6": the nonretained fraction corresponding to peak No. 1 of the chromatographic profile of FIG. 4,
lane "E7": the elution fraction corresponding to peak No. 2 of the chromatographic profile of FIG. 4,
lane "E8": the elution fraction collected downstream of peak No. 2 and upstream of peak No. 3 of the chromatographic profile of FIG. 4,
lane "T FIX": purified factor IX control.

The results represented in FIG. 5 confirm those of FIG. 4. These results illustrate that the chromatography substrate on which the aptamer is immobilized allows the specific purification of human factor IX from a complex medium such as a plasma fraction enriched in factor IX.

Furthermore, the results of the example illustrate the high degree of enrichment in human factor IX which is obtained after passing the starting product of complex composition over the affinity chromatography substrate on which the Mapt 2 aptamer of sequence SEQ ID NO: 86 is immobilized.

It can be concluded that the eluate exhibits a good electrophoretic purity with a considerable gain in purity compared with the starting product (>26-fold). The second band identified in the eluate certainly corresponds to another form of FIX.

Example 5

Method for Purifying Human Plasma Factor VII

A. Materials and Methods

A.1. Affinity Chromatography Substrate

Affinity gel material on which was immobilized the "Mapt-2 core" aptamer coupled directly to biotin, without a spacer chain between the aptamer and the biotin. The aptamer is immobilized on a streptavidin gel (supplier Novagen) by means of a 5'-terminal biotin, with a theoretical ligand density of 0.4 mg/ml: volume 1 ml.

The aptamer used is the Mapt-2 core aptamer of sequence SEQ ID NO: 20.

A.2. Starting Product

The starting product consists of a composition of human plasma factor VII purified to 98%.

A.3. Purification Protocol

Gel equilibration: 0.050 M Tris-HCl, 0.010 M $CaCl_2$, 0.05 mM $MgCl_2$, pH 7.5,
Elution: 0.020 M Tris-HCl, 0.010 M EDTA, pH 7.5.

240 µg of human plasma factor VII purified to 98% is injected with a flow rate of 0.5 ml/min in equilibration buffer.

After detection of the peak of nonretained material, 2 column volumes of elution buffer are injected.

The protein peaks are detected by measuring the value of absorbance at the wavelength of 280 nanometers.

B. Results

Figure 6:
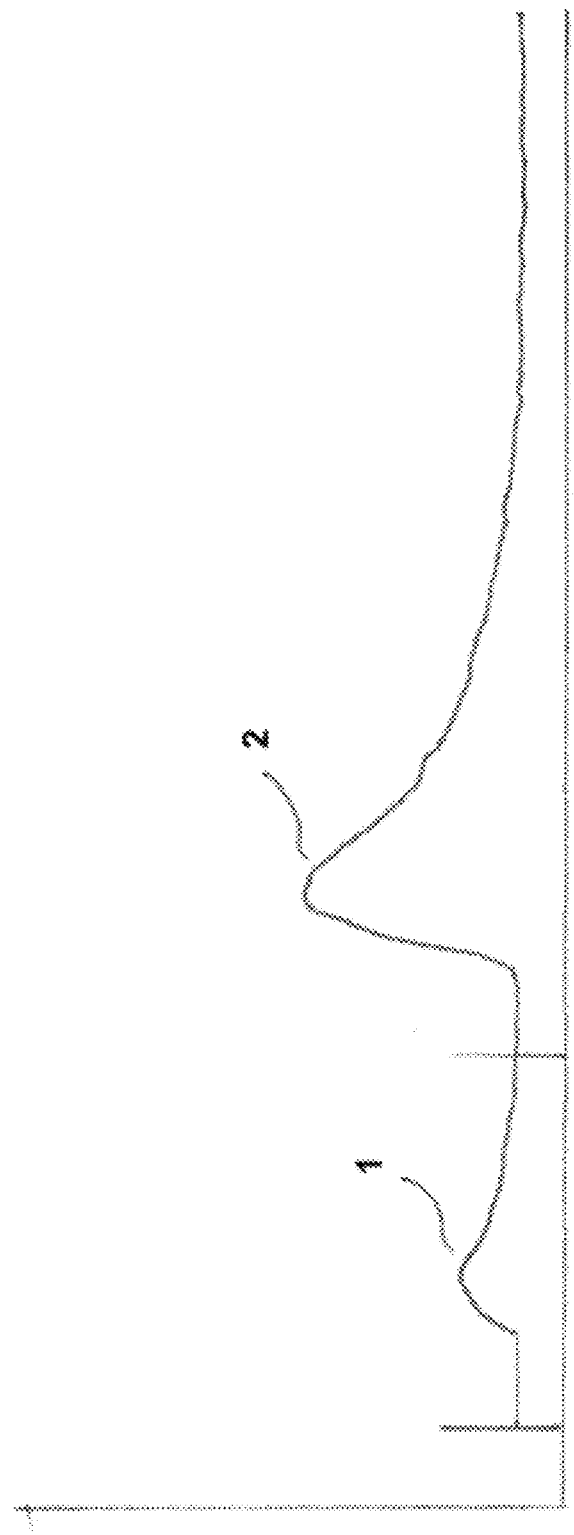
FIG. 6 represents the curve of the values of the measurement of absorbance at 280 nm as a function of time.
Figure 7:
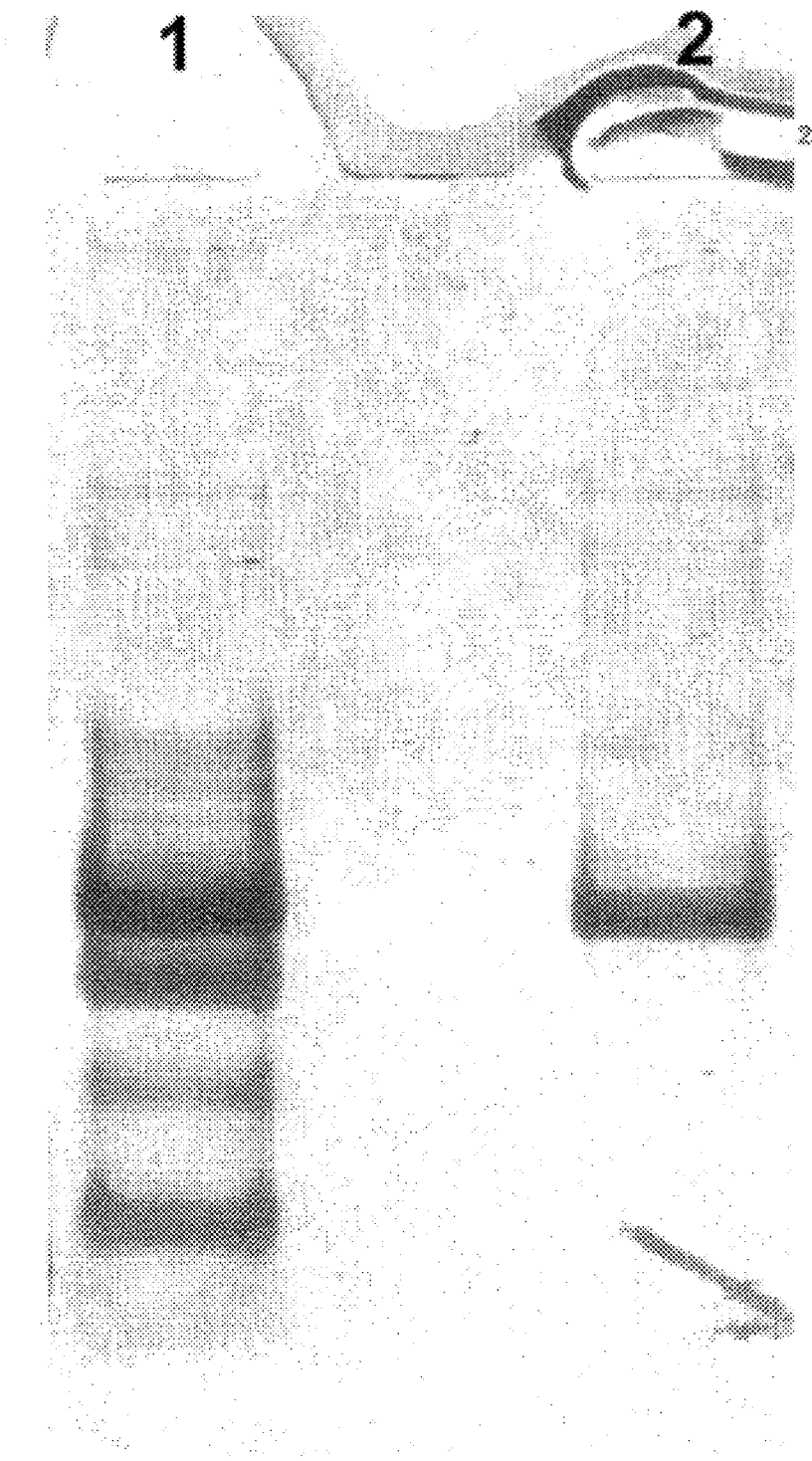
FIG. 7 represents an image of a gel of the starting product and also the eluted product, analyzed by SDS PAGE with silver nitrate staining in order to visualize the elimination of the impurities: lane No. 1 corresponds to the starting-product fraction and lane No. 2 to the elution fraction. Despite the considerable purity of the starting product, it is noted that the eluted fraction no longer contains any contaminants or degraded forms.

The results are illustrated in FIGS. 6 and 7.

FIG. 6 represents the curve of the values of the measurement of absorbance at 280 nm as a function of time. In FIG. 6, peak No. 1 corresponds to the fraction of the starting product which was not retained on the column. Peak No. 2 corresponds to the elution fraction.

The starting product and also the eluted product were analyzed by SDS PAGE with silver nitrate staining in order to visualize the elimination of the impurities. FIG. 7 represents this gel: lane No. 1 corresponds to the fraction of the starting product and lane No. 2 to the elution fraction. Despite the considerable purity of the starting product, it is noted that the eluted fraction no longer contains contaminants or degraded forms.

The results of FIGS. 6 and 7 show that the aptamer of sequence SEQ ID NO: 20 is capable of binding human FVII and of specifically eluting it in the presence of EDTA.

Example 6

Absence of Binding of the Aptamer to Rabbit FVII

A. Materials and Methods

A.1. Affinity Chromatography Substrate

Affinity gel coupled to streptavidin, on which the aptamer of sequence SEQ ID NO: 86 was immobilized by means of a spacer chain (supplier Novagen) via a 5'-terminal biotin, with a theoretical ligand density of 0.35 mg/ml: volume 1 ml.

The aptamer used is the aptamer of sequence SEQ ID NO: 86.

A.2. Starting Product

Eluate of hydroxyapatite enriched in rabbit FVII obtained by purification from rabbit plasma, contact time 10 minutes, flow rate 0.5 ml/min.

A.3. Purification Protocol

Gel equilibration: 0.050 M Tris-HCl, 0.010 M $CaCl_2$, 0.05 mM $MgSO_3$, pH 7.5,
Elution: 0.050 M Tris-HCl, 0.010 M EDTA, pH 7.5, 36 µg are injected into the gel with a contact time of 10 minutes. The elution is carried out by injecting 2 ml of elution buffer.

The protein peaks are detected by measuring the value of absorbance at the wavelength of 280 nanometers.

A.4. Protocols for Analysis of the Fractions in Terms of Proteins and in Terms of Factor VII The fractions are analyzed for their amidolytic activity by chromogenic assay using a Stago kit according to the supplier's recommendations (factor VIIa StatClot kit). The amidolytic activity is then converted to µg of FVII contained in said fraction.

B. Results

The results are illustrated in table 4 below.

TABLE 4

| Steps | Proteins (mg/ml) | FVIIam (IU/ml) | Volume (ml) | Amount FVII (µg) | Purity (%) | Step yield (%) |
|---|---|---|---|---|---|---|
| Starting material | 1.38 | 57 | 2.5 | 71 | 2% | 100% |
| Dialyzed eluate | 0.97 | 21.8 | 3.4 | 36.7 | 1% | 52% |
| Mapt-2 eluate | NA | 0.04 | 4.0 | 0.08 | NA | 0.2% |

The results in table 4 show that the rabbit factor VII is not retained on the affinity gel on which the Mapt-2 aptamer is immobilized.

Example 7

Specific Embodiments of a Protocol for Interaction of Human Factor VII with an Aptamer on Biacore (Resistance to NaCl)

A. Materials and Methods

A solid substrate on which molecules of the nucleic aptamer of the invention of sequence SEQ ID NO: 86, also denoted herein "Mapt2", were immobilized was produced. Prior to its binding to the solid substrate, the 5' end of the Mapt2 aptamer was chemically coupled to a spacer chain consisting of 4 molecules of PEG(C18). Then, the free end of the spacer chain, opposite the end coupled to the aptamer, was coupled to a biotin molecule.

A solid substrate containing immobilized streptavidin molecules is provided (series S sensor Chip SA, GE).

The solid substrate above was then brought into contact with the aptamer compounds above in order to immobilize the nucleic acids of sequence SEQ ID NO: 86, by noncovalent association between the streptavidin molecules of the substrate and the biotin molecules of the aptamer compounds.

The Mapt2 aptamer is thus immobilized with a degree of immobilization of 3772 RU (1 RU corresponds approximately to 1 pg of immobilized product per $mm^2$).

Purified transgenic human FVII obtained from transgenic rabbit milk (FVII HPTG, purity: 98%) was diluted in running buffer (50 mM Tris, 50 mM NaCl, 10 mM $CaCl_2$, 4 mM $MgCl_2$, pH 7.4) so as to obtain a sample having an FVII concentration of 200 mM.

The sample was injected onto the chip (solid substrate) containing the Mapt2 aptamer immobilized by means of a biotin-streptavidin interaction. Next, buffers containing an increasing concentration of NaCl were injected onto the solid substrate (3 series of injections ranging from 1 M NaCl to 3 M NaCl). All the injections were carried out with a flow rate of 30 μl/min for 60 sec after the injection. After the 3 series of injections with the 3 buffers containing NaCl, elution buffer (10 mM EDTA) was then injected for 75 sec with a flow rate of 30 μl/min in order to detach the FVII HPTG from the aptamer.

These analyses are carried out with the RPS Biacore T100 apparatus (GE). The modeling of the interactions recorded is carried out by means of the Biaevaluation software (GE).

The curves of binding of the Mapt2 immobilized aptamer to the transgenic human FVII were calculated with the dedicated module of the Biacore® control software, version 1.2.

The results of binding of the Mapt2 aptamer to human FVII made it possible to determine that the binding of the Mapt2 aptamer to human FVII is not detrimentally modified by the injection of the buffers containing NaCl.

B. Results

Figure 8:
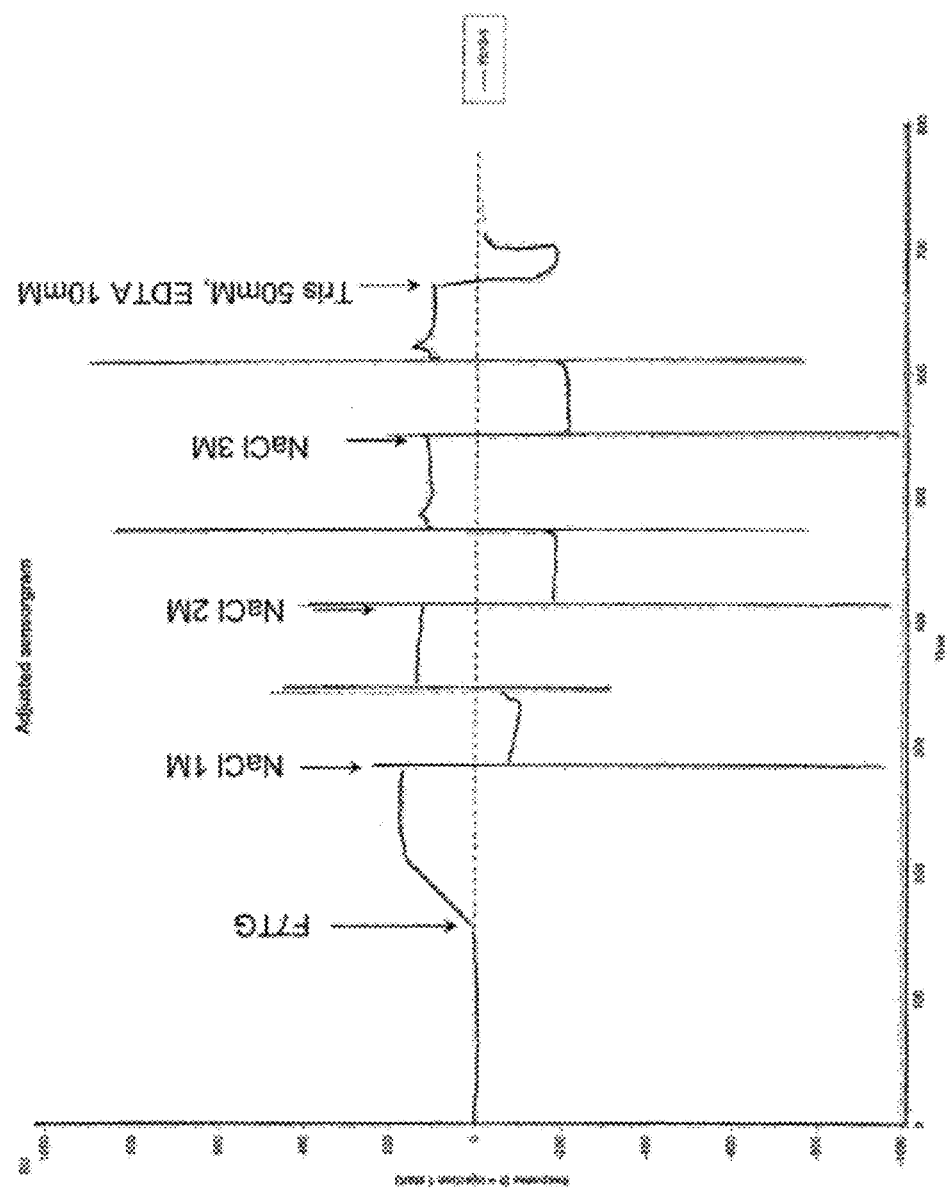
FIG. 8 represents the curves of binding of the Mapt2 immobilized aptamer to the recombinant human factor VII produced in the milk of a transgenic rabbit. The arrows correspond to the time of the various injections, respectively from left to right on FIG. 8: 1: injection of recombinant factor VII; 2: injection of a buffer containing 1M NaCl; 3: injection of a buffer containing 2M NaCl; 4: injection of a buffer containing 3M NaCl; 5: injection of a 50 mM Tris buffer containing 10 mM EDTA. Along the x-axis: the time expressed in seconds; along the y-axis: the value of the response signal, expressed in arbitrary units (RU).

The results are illustrated in FIG. 8.

Example 8

Specific Embodiments of a Protocol for Interaction of Human Factor VII with an Aptamer on Biacore (Resistance to Propylene Glycol)

A. Materials and Methods

A solid substrate on which molecules of the nucleic aptamer of the invention of sequence SEQ ID NO: 86, also denoted herein "Mapt2", were immobilized was produced. Prior to its binding to the solid substrate, the 5' end of the Mapt2 aptamer was chemically coupled to a spacer chain consisting of 4 molecules of PEG(C18). Then, the free end of the spacer chain, opposite the end coupled to the aptamer, was coupled to a biotin molecule.

A solid substrate containing immobilized streptavidin molecules is provided (series S sensor Chip SA, GE).

The solid substrate above was then brought into contact with the aptamer compounds above in order to immobilize the nucleic acids of sequence SEQ ID NO: 86, by noncovalent association between the streptavidin molecules of the substrate and the biotin molecules of the aptamer compounds.

The Mapt2 aptamer is thus immobilized with a degree of immobilization of 5319 RU (1 RU corresponds approximately to 1 pg of immobilized product per $mm^2$).

Purified transgenic human FVII obtained from transgenic rabbit milk (FVII HPTG, purity: 98%) was diluted in running buffer (50 mM Tris, 10 mM $CaCl_2$, 4 mM $MgCl_2$, pH 7.4) so as to obtain a sample with an FVII concentration of 200 mM.

The sample was injected onto the chip (solid substrate) containing the Mapt2 aptamer immobilized by means of a biotin-streptavidin interaction. Next, a buffer containing 50% propylene glycol was injected onto the solid substrate. All the injections were carried out with a flow rate of 30 μl/min for 60 sec after the injection. After the injection with the buffer containing 50% propylene glycol, elution buffer (10 mM EDTA) was then injected for 75 sec with a flow rate of 30 μl/min in order to detach the FVII HPTG from the aptamer.

These analyses are carried out with the RPS Biacore T100 apparatus (GE). The modeling of the interactions recorded is carried out by means of the Biaevaluation software (GE).

The curves of binding of the Mapt2 immobilized aptamer to the transgenic human FVII were calculated with the dedicated module of the Biacore® control software, version 1.2.

The results of binding of the Mapt2 aptamer to human FVII made it possible to determine that the binding of the Mapt2 aptamer to human FVII is not detrimentally modified by the injection of the buffer containing propylene glycol.

B. Results

The results are illustrated in FIG. 9.

The invention claimed is:

1. An affinity substrate for selectively purifying a blood plasma protein from a complex medium by chromatography, comprising at least a non-covalent complex between (i) a deoxyribonucleic aptamer; and (ii) a blood plasma protein, wherein said deoxyribonucleic aptamer is covalently immobilized on a solid substrate material, wherein the deoxyribonucleic aptamer binds specifically to said blood plasma protein, and wherein said non-covalent complex is dissociated in the presence of a divalent-ion-chelating agent.

2. The affinity substrate of claim 1, wherein said deoxyribonucleic aptamer is included in the structure of a compound of formula (I) below:

[FIX]$_x$-[SPAC]$_y$-[APT]   (I), in which:

[FIX] signifies a compound for immobilization on a solid substrate material,
[SPAC] signifies a spacer chain,
[APT] signifies a deoxyribonucleic acid which binds specifically to a plasma protein,
x is an integer equal to 0 or 1, and
y is an integer equal to 0 or 1.

3. The affinity substrate of claim 1, wherein the blood plasma protein is selected from the group consisting of albumin, alpha/macroglobulin, antichymotrypsin, antithrombin, antitrypsin, Apo A, Apo B, Apo C, Apo D, Apo E, Apo F, Apo G, beta XIIa, C1-inhibitor, C-reactive protein, C7, Clr, Cls, C2, C3, C4, C4bP, C5, C6, Clq, C8, C9, carboxypeptidase N, ceruloplasmin, factor B, factor D, factor H, factor I, factor IX, factor V, factor VII, factor VIIa, factor VIII, factor X, factor XI, factor XII, factor XIII, fibrinogen, fibronectin, haptoglobin, hemopexin, heparin cofactor II, histidine-rich GP, IgA, IgD, IgE, IgG, IT1, IgM, kininase II, kininogen HPM, lysozyme, PAI 2, PAI 1, PCI, plasmin, plasmin inhibitor, plasminogen, prealbumin, prokallikrein, properdin, protease nexin INH, protein C, protein S, protein Z, prothrombin, TFPI, thiol-proteinase, thrombomodulin, tissue factor (TF), TPA, transcolabamin II, transcortin, transferrin, vitronectin and von Willebrand factor.

4. The affinity substrate of claim 1, wherein the blood plasma protein consists of a coagulation protein selected from the group consisting of factor I (fibrinogen), factor II (prothrombin), factor V (proaccelerin), factor VII (proconvertin), factor VIII (antihemophilic factor A), factor IX (anti-hemophilic factor B), factor X (Stuart factor), factor XI (Rosenthal factor or PTA), factor XII (Hageman factor), factor XIII (fibrin-stabilizing factor or FSF), PK (Prekallikrein), HMWK (high-molecular-weight kininogen), tissue thromboplastin, heparin cofactor II (HCII), protein C (PC), thrombomodulin (TM), protein S (PS), von Willebrand factor (vWF) and tissue factor pathway inhibitor (TFPI), and tissue factors.

5. The affinity substrate of claim 1, wherein said divalent-ion-chelating agent is EDTA.

6. The affinity substrate of claim 1, wherein the blood plasma protein is human.

7. The affinity substrate of claim 1, wherein the solid substrate material is selected from the group consisting of resins, polymer beads, magnetic beads, paramagnetic beads, substrate materials of filter membranes, and polymer materials.

8. The affinity substrate of claim 2, wherein the solid substrate material is selected from the group consisting of resins, polymer beads, magnetic beads, paramagnetic beads, substrate materials of filter membranes, and polymer materials.

9. An affinity substrate for selectively purifying a blood plasma protein from a complex medium by chromatography, comprising at least a non-covalent complex between (i) a deoxyribonucleic aptamer; and (ii) a blood plasma protein, wherein the deoxyribonucleic aptamer is immobilized on a solid substrate material, wherein the deoxyribonucleic aptamer specifically binds to a human blood plasma protein, but does not bind to non-human blood plasma protein homologous to said human blood plasma protein, and wherein the non-covalent complex is dissociated in the presence of a divalent-ion-chelating agent.

10. An affinity substrate for selectively purifying a blood plasma protein from a complex medium by chromatography, comprising at least a non-covalent complex between (i) a deoxyribonucleic aptamer; and (ii) a blood plasma protein, wherein the blood plasma protein is a human coagulation protein, wherein the deoxyribonucleic aptamer is immobilized on a solid substrate material, wherein the deoxyribonucleic aptamer binds specifically to said blood plasma protein, and wherein the non-covalent complex is dissociated in the presence of a divalent-ion-chelating agent.

11. The affinity substrate of claim 2 wherein [SPAC] is selected from nonspecific oligonucleotides and polyethylene glycol.

12. An affinity substrate, comprising a non-covalent complex between (i) a deoxyribonucleic aptamer, and (ii) a human blood plasma protein,
  wherein the deoxyribonucleic aptamer binds specifically to the human blood plasma protein,
  wherein the deoxyribonucleic aptamer does not bind to a non-human blood plasma protein homologous to said human blood plasma protein,
  wherein the deoxyribonucleic aptamer is covalently immobilized on a solid substrate material,
  wherein the non-covalent complex is dissociated in the presence of a divalent-ion-chelating agent, and
  wherein the affinity substrate is for selectively purifying the human blood plasma protein by chromatography at an industrial scale from a complex medium which may contain the non-human blood plasma protein.

13. An affinity chromatography device comprising a container and the affinity substrate of claim 1, wherein the affinity substrate is present within the container in an amount sufficient for selectively purifying the blood plasma protein.

14. An affinity chromatography device comprising a container and the affinity substrate of claim 12, wherein the affinity substrate is present within the container in an amount sufficient for selectively purifying the human blood plasma protein.

* * * * *